(12) United States Patent
Bennett et al.

(10) Patent No.: US 8,980,853 B2
(45) Date of Patent: Mar. 17, 2015

(54) COMPOSITIONS AND METHODS FOR MODULATION OF SMN2 SPLICING IN A SUBJECT

(75) Inventors: C. Frank Bennett, Carlsbad, CA (US); Gene Hung, San Diego, CA (US); Frank Rigo, Carlsbad, CA (US); Adrian R. Krainer, Huntington Square, NY (US); Yimin Hua, Jericho, NY (US); Marco A. Passini, Shrewsbury, MA (US); Lamya Shihabuddin, Brighton, MA (US); Seng H. Cheng, Natick, MA (US); Katherine W. Klinger, Sudbury, MA (US)

(73) Assignees: Isis Pharmaceuticals, Inc., Carlsbad, CA (US); Cold Spring Harbor Laboratory, Cold Spring Harbor, NY (US)

( * ) Notice: Subject to any disclaimer, the term of this patent is extended or adjusted under 35 U.S.C. 154(b) by 160 days.

(21) Appl. No.: 13/380,021

(22) PCT Filed: Jun. 17, 2010

(86) PCT No.: PCT/US2010/039077
§ 371 (c)(1), (2), (4) Date: Apr. 12, 2012

(87) PCT Pub. No.: WO2010/148249
PCT Pub. Date: Dec. 23, 2010

(65) Prior Publication Data
US 2012/0190728 A1    Jul. 26, 2012

Related U.S. Application Data

(60) Provisional application No. 61/218,031, filed on Jun. 17, 2009.

(51) Int. Cl.
| | |
|---|---|
| A61K 31/70 | (2006.01) |
| C07H 21/02 | (2006.01) |
| C07H 21/04 | (2006.01) |
| A61K 31/7088 | (2006.01) |
| C12N 15/113 | (2010.01) |
| C12Q 1/68 | (2006.01) |
| A61K 31/712 | (2006.01) |

(52) U.S. Cl.
CPC ........... *A61K 31/7088* (2013.01); *A61K 31/712* (2013.01); *C12N 15/113* (2013.01); *C12N 2310/11* (2013.01); *C12N 2320/33* (2013.01)
USPC ........ 514/44 A; 536/23.1; 536/24.5; 536/24.1

(58) Field of Classification Search
None
See application file for complete search history.

(56) References Cited

U.S. PATENT DOCUMENTS

| | | | |
|---|---|---|---|
| 5,176,996 A | 1/1993 | Hogan et al. | |
| 5,256,775 A | 10/1993 | Froehler | |
| 5,294,564 A | 3/1994 | Karapiperis et al. | |
| 5,627,274 A | 5/1997 | Kole et al. | |
| 5,801,154 A | 9/1998 | Baracchini et al. | |
| 6,172,216 B1 | 1/2001 | Bennett et al. | |
| 6,214,986 B1 | 4/2001 | Bennett et al. | |
| 6,376,508 B1 | 4/2002 | Li et al. | |
| 6,582,908 B2 | 6/2003 | Fodor et al. | |
| 6,753,423 B1 | 6/2004 | Cook et al. | |
| 6,770,633 B1 | 8/2004 | Robbins et al. | |
| 6,962,906 B2 | 11/2005 | Efimov et al. | |
| 7,034,009 B2 | 4/2006 | Pavco et al. | |
| 7,053,207 B2 | 5/2006 | Wengel | |
| 7,838,657 B2 | 11/2010 | Singh et al. | |
| 8,110,560 B2* | 2/2012 | Singh et al. | 514/44 R |
| 8,361,977 B2* | 1/2013 | Baker et al. | 514/44 A |
| 8,586,559 B2 | 11/2013 | Singh et al. | |
| 2001/0053519 A1 | 12/2001 | Fodor et al. | |
| 2003/0228597 A1 | 12/2003 | Cowsert et al. | |
| 2007/0031844 A1 | 2/2007 | Khvorova et al. | |
| 2007/0292408 A1 | 12/2007 | Singh et al. | |
| 2007/0299021 A1 | 12/2007 | Dunckley et al. | |
| 2008/0045456 A1 | 2/2008 | Greenway et al. | |
| 2010/0087511 A1* | 4/2010 | Singh et al. | 514/44 R |
| 2012/0149757 A1 | 6/2012 | Krainer et al. | |
| 2013/0109091 A1 | 5/2013 | Baker et al. | |

FOREIGN PATENT DOCUMENTS

| | | |
|---|---|---|
| WO | WO 94/26887 | 11/1994 |
| WO | WO 95/22980 | 8/1995 |
| WO | WO 01/09311 | 2/2001 |
| WO | WO 02/38738 | 5/2002 |
| WO | WO 2004/113867 | 12/2004 |
| WO | WO 2007/002390 | 1/2007 |
| WO | WO 2010/091308 | 8/2010 |

OTHER PUBLICATIONS

Hua et al., "Antisense correction of SMN2 splicing in the CNS rescues necrosis in a type III SMA mouse model" Genes Dev. (2010) 24:1634-1644.
Batrakova et al., "Mechanism of Pluronic Effect on P-Glycoprotein Efflux System in Blood-Brain Barrier: Contributions of Energy Depletion and Membrane Fluidization" The Journal of Pharmacology and Experimental Therapeutics (2001) 299(2):483-493.
Branch et al., "A good antisense molecule is hard to find," TIBS (1998) 23:45-50.
Brichta et al., "Valproic acid increases the SMN2 protein level: a well-known drug as a potential therapy for spinal muscular atrophy" Human Molecular Genetics (2003) 12(19):2481-2489.

(Continued)

*Primary Examiner* — Sean McGarry
(74) *Attorney, Agent, or Firm* — Knobbe Martens LLC

(57) ABSTRACT

Disclosed herein are compounds, compositions and methods for modulating splicing of SMN2 mRNA in a subject. Also provided are uses of disclosed compounds and compositions in the manufacture of a medicament for treatment of diseases and disorders, including spinal muscular atrophy.

4 Claims, 13 Drawing Sheets

(56) References Cited

OTHER PUBLICATIONS

Categni et al., "Correction. Of disease-associated exon skipping by synthetic exon-specific activators" Nat. Struct. Biol. (2003) 10:120-125.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Crooke, "Antisense strategies" Curr. Mol. Med. (2004) 4(5):465-487.

Dokka et al., "Novel non-endocyte delivery of antisense oligonucleotides" Advanced Drug Delivery Reviews (2000) 44:35-49.

Dominski et al., "Restoration of correct splicing in thalassemic pre-mRNA by antisense oligonucleotides" PNAS (1993) 90:8673-8677.

Dunckley et al., "Modification of splicing in the dystrophin gene in cultured mdx muscle cells by antisense oligoribonucleotides" Human Mol. Genetics (1998) 7(7):1083-1090.

Dunckley et al., "Modulation of Splicing in the DMD Gene by Antisense Oligoribonucleotides" Nucleosides & Nucleotides (1997) 16(7-9):1665-1668.

Efimov et al., "Phosphono Peptide Nucleic Acids with a Constrained Hydroxyproline-Based Backbone" Nucleosides, Nucleotides & Nucleic Acids (2003) 22(5-8):593-599.

Forte et al., "Small interfering RNAs and Antisense Oligonucleotides for Treatment of Neurological Diseases" Current Drug Targets (2005) 6:21-29.

Friedman et al., "Correction of Aberrant Splicing of the Cystic Fibrosis Transmembrane Conductance Regulator (CFTR) Gene by Antisense Oligonucleotides" J. Biol. Chem. (1999) 274:36193-36199.

Heasman, "Morpholino Oligos: Making Sense of Antisense?" Developmental Biology (2002) 243:209-214.

Hofmann et al., "Htra2-beta1 stimulates an exonic splicing enhancer and can restor full-length SMN expression to survival motor neuron 2 (SMN2)" PNAS (2000) 97(17):9618-9623.

Hua et al., "Enhancement of SMN2 exon 7 inclusion by antisense oligonucleotides targeting the exon" PLOS Biology (2007) 5(4):E73.

Ittig et al., "Nuclear antisense effects in cyclophilin A pre-mRNA splicing by oligonucleotides: a comparison of tricyclo-DNA with LNA" Nucleic Acids Research (2004) 32(10:346-353.

Jaeger et al., "Transport of Antisense Across the Blood-Brain Barrier" Methods in Molecular Medicine (2005) vol. 106: Antisense Therapeutics, Second Edition, I. Phillips (Ed.) Humana Press, Inc. Totowa, N.J., Cht. 12:237-251.

Kashima et al., "A negative element in SMN2 exon 7 inhibits splicing in spinal muscular atrophy." Nature Genetics (2003) 34(4):460-463.

Kole, "Modification ot pre-mRNA splicing by antisense oligonucleotides" Acta Biochimica Polonica (1997) 44(2):231-238.

Kole et al., "RNA modulation, repair and remodeling by splice switching oligonucleotides" Acta Biochimica Polonica (2004) 51(2):373-378.

Kurreck, "Antisense Technologies Improvement Through Novel Chemical Modifications" European Journal of Biochemistry (2003) 270(8):1628-1644.

Lacerra et al., "Restoration of hemoglobin A synthesis in erythroid cells from peripheral blood of thalassemic patients" PNAS (2000) 97(17):9591-9596.

Lefebvre et al., "The Role of the SMN Gene in Proximal Spinal Muscular Atrophy" Hum. Mol. Genet. (1998) 7(10):1531-1536.

Lim et al., "Modulation of Survival Motor Neuron Pre-mRNA Splicing by Inhibition of Alternative 3'Splice Site Pairing" J. Biol. Chem. (2001) 276(48):45476-45483.

Lorson et al., "A single nucleotide in the SMN gene regulates splicing and is responsible for spinal muscular atrophy" PNAS (1999) 96:6307-6311.

Lu et al., "Systemic delivery of antisense oligoribonucleotide restores dystrophin expression in body-wide skeletal muscles" PNAS (2005) 102(1):198-203.

Madocsai et al., "Correction of SMN2 Pre-mRNA Splicing by Antisense U7 Small Nuclear RNAs" Molecular Therapy (2005) 12(6):1013-1022.

Miyajima et al., "Identification of a Cis-Acting Element for the Regulation of SMN Exon 7 Splicing" J. Biol. Chem. (2002) 277(26):23271-23277.

Miyaso et al., "An Intronic Splicing Enhancer Element in Survival Motor Neuron (SMN) Pre-mRNA" J. Biol. Chem. (2003) 278(18):15825-15831.

New England Biolabs 1998/99 Catalog (cover page and pp. 121 and 284).

Rebuffat et al., "Gene delivery by a steroid-peptide nucleic acid conjugate" FASEB J. (2002) 19(11):1426-1428.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Sazani et al., "Therapeutic potential of antisense oligonucleotides as modulators of alternative splicing" The Journal of Clinical Investigation (2003) 112(4):481-486.

Sierakowska et al., "Restoration of β-Globin Gene Expression in Mammalian Cells by Antisense Oligonucleotides That Modify the Aberrant Splicing Patierns of Thalassemic Pre-mRNAs" Nucleosides & Nucleotides (1997) 16(7-9):1173-1182.

Sierakowska et al., "Repair of thalassemic human β-globin mRNA in mammalian cells by antisense oligonucleotides" PNAS (1996) 93:12840-12844.

Singh et al., "In vivo selection reveals combinatorial controls that define a critical exon in the spinal muscular atrophy genes" RNA (2004) 10:1291-1305.

Singh et al., "An extended inhibitory context causes skipping of exon 7 of SMN2 in spinal muscular atrophy" Biochem. Biophys. Res. Comm. (2004) 315(2):381-388.

Singh et al., "Splicing of a critical exon of human Survival Motor Neuron is regulated by a unique silencer element located in the last intron" Molecular and Cellular Biology (2006) 26(4):1333-1346.

Skordis et al., "Bifunctional Antisense Oligonucleotides Provide a Trans-Acting Splicing Enhancer that Stimulated SMN2 Gene Expression in Patient Fibroblasts" PNAS (2003) 100(7):4114-4119.

Takeshima et al., "Modulation of in vitro splicing of the upstream intron by modifying an intra-exon sequence which is deleted from the dystrophin gene in dystrophin Kobe." J. Clin. Invest. (1995) 95(2):515-520.

Taylor et al., "Induction of endogenous Bcl-xS through the control of Bcl-x pre-mRNA splicing by antisense oligonucleotides" Nat. Biotechnol. (1999) 17:1097-1100.

Veldink et al., "SMN genotypes producing less SMN protein increase susceptibility to and severity of sporadic ALS" Neurology (2005) 65(6):820-825.

Vinogradov et al., "Nanogels for Oligonucleotide Delivery to the Brain" Bioconjugate Chem. (2004) 15:50-60.

Wahlestedt et al., "Potent and nontoxic antisense oligonucleotides containined locked nucleic acids" PNAS (2000) 97(10):5633-5638.

Wang, "Antisense oligodeoxynucleotides selectively suppress expression of the mutant alpha 2(I) collagen allele in type IV osteogenesis imperfecta fibroblasts. A molecular approach to therapeutics of dominant negative disorders." J. Clin. Invest. (1996) 97(2):448-454.

Wilton et al., "Specific removal of the nonsense mutation from the mdx dystrophin mRNA using antisense oligonucleotides" Neuromuscul. Disord (1999) 9:330-338.

European Search Reprot for application EP 06773838 dated Aug. 11, 2010.

International Search Report for application PCT/US06/24469 dated Sep. 13, 2007.

International Search Report for application PCT/US10/30940 dated Jul. 13, 2010.

International Search Report for application PCT/US2010/39077 dated Aug. 17, 2010.

(56) References Cited

OTHER PUBLICATIONS

Baughan et al., "Delivery of bifunctional RNAs tha target an intronic repressor and increase SMN levels in an animal model of spinal muscular atrophy" Human Molecular Genetics (2009) 18(9):1600-1611.

Hua et al., "Antisense masking of an hnRNP A1/A2 inronic splicing silencer corrects SMN2 splicing in transgenic mice" American Journal of Human Genetics (2008) 82(4):834-848.

Le et al., "SMNdelta7, the major product of the centromeric survival motor neuron (SMN2) gene, exends survival in mice with spinal muscular atrophy and associates with full-length SMN" Human Molecular Genetics (2005) 14(6):845-857.

Schmid et al., "Animal models of spinal muscular atrophy" Journal of Child Neurology (2007) 22(8):1004-1012.

Williams et al., "Oligonucleotide-mediated survival of motor neuron protein expression in CNS improves phenotype in a mouse model of Spinal Muscular Atrophy" Journal of Neuroscience (2009) 29(24):76-33-7638.

European Search Report for application EP 10790221 dated Sep. 4, 2013.

* cited by examiner

A

B

ASO Treatment Increases Motor Neuron Cell Counts in the Spinal Cord

4 μg dose, 16 days post-injection

COMPOSITIONS AND METHODS FOR MODULATION OF SMN2 SPLICING IN A SUBJECT

SEQUENCE LISTING

The present application is being filed along with a Sequence Listing in electronic format. The Sequence Listing is provided as a file entitled 20100617_CORE0086WOSEQ.txt, created Jun. 17, 2010, which is 5 Kb in size. The information in the electronic format of the sequence listing is incorporated herein by reference in its entirety.

BACKGROUND OF THE INVENTION

Newly synthesized eukaryotic mRNA molecules, known as primary transcripts or pre-mRNA are processed before translation. Processing of the pre-mRNAs includes addition of a 5' methylated cap and an approximately 200-250 base poly(A) tail to the 3' end of the transcript. Processing of mRNA from pre-mRNA also frequently involves splicing of the pre-mRNA, which occurs in the maturation of 90-95% of mammalian mRNAs. Introns (or intervening sequences) are regions of a pre-mRNA (or the DNA encoding it) that are not included in the coding sequence of the mature mRNA. Exons are regions of a primary transcript that remain in the mature mRNA. The exons are spliced together to form the mature mRNA sequence. Splice junctions are also referred to as splice sites with the 5' side of the junction often called the "5' splice site," or "splice donor site" and the 3' side the "3' splice site" or "splice acceptor site." In splicing, the 3' end of an upstream exon is joined to the 5' end of the downstream exon. Thus the unspliced pre-mRNA has an exon/intron junction at the 5' end of an intron and an intron/exon junction at the 3' end of an intron. After the intron is removed, the exons are contiguous at what is sometimes referred to as the exon/exon junction or boundary in the mature mRNA. Cryptic splice sites are those which are less often used but may be used when the usual splice site is blocked or unavailable. Alternative splicing, defined as the splicing together of different combinations of exons, often results in multiple mRNA transcripts from a single gene.

Up to 50% of human genetic diseases resulting from a point mutation result in aberrant pre-mRNA processing. Such point mutations can either disrupt a current splice site or create a new splice site, resulting in mRNA transcripts comprised of a different combination of exons or with deletions in exons. Point mutations also can result in activation of a cryptic splice site or disrupt regulatory cis elements (i.e. splicing enhancers or silencers) (Cartegni et al., Nat. Rev. Genet., 2002, 3, 285-298; Drawczak et al., Hum. Genet., 1992, 90, 41-54). Antisense oligonucleotides have been used to target mutations that lead to aberrant splicing in several genetic diseases in order to redirect splicing to give a desired splice product (Kole, Acta Biochimica Polonica, 1997, 44, 231-238).

Antisense compounds have also been used to alter the ratio of naturally occurring alternate splice variants such as the long and short forms of Bcl-x pre-mRNA (U.S. Pat. No. 6,172,216; U.S. Pat. No. 6,214,986; Taylor et al., Nat. Biotechnol. 1999, 17, 1097-1100) or to force skipping of specific exons containing premature termination codons (Wilton et al., Neuromuscul. Disord., 1999, 9, 330-338). U.S. Pat. No. 5,627,274 and WO 94/26887 disclose compositions and methods for combating aberrant splicing in a pre-mRNA molecule containing a mutation using antisense oligonucleotides which do not activate RNAse H.

Proximal spinal muscular atrophy (SMA) is a genetic, neurodegenerative disorder characterized by the loss of spinal motor neurons. SMA is an autosomal recessive disease of early onset and is currently the leading cause of death among infants. The severity of SMA varies among patients and has thus been classified into three types. Type I SMA is the most severe form with onset at birth or within 6 months and typically results in death within 2 years. Children with type I SMA are unable to sit or walk. Type II SMA is the intermediate form and patients are able to sit, but cannot stand or walk. Patients with type III SMA, a chronic form of the disease, typically develop SMA after 18 months of age (Lefebvre et al., Hum. Mol. Genet., 1998, 7, 1531-1536).

The molecular basis of SMA is caused by the loss of both copies of survival motor neuron gene 1 (SMN1), which may also be known as SMN Telomeric, a protein that is part of a multi-protein complex thought to be involved in snRNP biogenesis and recycling. A nearly identical gene, SMN2, which may also be known as SMN Centromeric, exists in a duplicated region on chromosome 5q13 and modulates disease severity. Expression of the normal SMN1 gene results solely in expression of survival motor neuron (SMN) protein. Although SMN1 and SMN2 have the potential to code for the same protein, SMN2 contains a translationally silent mutation at position +6 of exon 7, which results in inefficient inclusion of exon 7 in SMN2 transcripts. Thus, the predominant form of SMN2 is a truncated version, lacking exon 7, which is unstable and inactive (Cartegni and Krainer, Nat. Genet., 2002, 30, 377-384). Expression of the SMN2 gene results in approximately 10-20% of the SMN protein and 80-90% of the unstable/non-functional SMNdelta7 protein. SMN protein plays a well-established role in assembly of the spliceosome and may also mediate mRNA trafficking in the axon and nerve terminus of neurons.

Antisense technology is an effective means for modulating the expression of one or more specific gene products, including alternative splice products, and is uniquely useful in a number of therapeutic, diagnostic, and research applications. The principle behind antisense technology is that an antisense compound, which hybridizes to a target nucleic acid, modulates gene expression activities such as transcription, splicing or translation through one of a number of antisense mechanisms. The sequence specificity of antisense compounds makes them extremely attractive as tools for target validation and gene functionalization, as well as therapeutics to selectively modulate the expression of genes involved in disease.

Certain antisense compounds complementary to SMN2 are known in the art. See for example, WO 2007/002390; U.S. 61/168,885; Hua et al., American J. of Human Genetics (April 2008) 82, 1-15; Singh et al., RNA Bio. 6:3, 1-10 (2009). Certain antisense compounds and methods disclosed herein posses desirable characteristics compared to such compounds and methods known in the art. Chimeric peptide nucleic acid molecules designed to modulate splicing of SMN2 have been described (WO 02/38738; Cartegni and Krainer, Nat. Struct. Biol., 2003, 10, 120-125).

SUMMARY OF THE INVENTION

In certain embodiments, the present invention provides methods comprising administering to a subject an antisense compound comprising an antisense oligonucleotide complementary to intron 7 of a nucleic acid encoding human SMN2 pre-mRNA, wherein the antisense compound is administered into the cerebrospinal fluid. In certain embodiments, the administration is into the intrathecal space. In certain embodiments, the administration is into the cerebrospinal fluid in the brain. In certain embodiments, the administration comprises a bolus injection. In certain embodiments, the administration comprises infusion with a delivery pump.

In certain embodiments, the antisense compound is administered at a dose from 0.01 to 10 milligrams of antisense compound per kilogram of body weight of the subject. In certain embodiments, the dose is from 0.01 to 10 milligrams of antisense compound per kilogram of body weight of the subject. In certain embodiments, the dose is from 0.01 to 5 milligrams of antisense compound per kilogram of body weight of the subject. In certain embodiments, the dose is from 0.05 to 1 milligrams of antisense compound per kilogram of body weight of the subject. In certain embodiments, the dose is from 0.01 to 0.5 milligrams of antisense compound per kilogram of body weight of the subject. In certain embodiments, the dose is from 0.05 to 0.5 milligrams of antisense compound per kilogram of body weight of the subject.

In certain embodiments, the dose is administered daily. In certain embodiments, the dose is administered weekly. In certain embodiments, the antisense compound is administered continuously and wherein the dose is the amount administered per day. In certain embodiments, the method comprises administering at least one induction dose during an induction phase and administering at least one maintenance dose during a maintenance phase. In certain embodiments, the induction dose is from 0.05 to 5.0 milligrams of antisense compound per kilogram of body weight of the subject. In certain embodiments, the maintenance dose is from 0.01 to 1.0 milligrams of antisense compound per kilogram of body weight of the subject. In certain embodiments, the duration of the induction phase is at least 1 week. In certain embodiments, the duration of the maintenance phase is at least 1 week. In certain embodiments, each induction dose and each maintenance dose comprises a single injection. In certain embodiments, each induction dose and each maintenance dose independently comprise two or more injections. In certain embodiments, antisense compound is administered at least 2 times over a treatment period of at least 1 week. In certain embodiments, the treatment period is at least one month. In certain embodiments, the treatment period is at least 2 months. In certain embodiments, the treatment period is at least 4 months. In certain embodiments, the induction dose is administered by one or more bolus injections and the maintenance dose is administered by an infusion pump.

In certain embodiments, the method comprises assessing the tolerability and/or effectiveness of the antisense compound. In certain embodiments, dose amount or frequency of antisense compound is reduced following an indication that administration of the antisense compound is not tolerated. In certain embodiments, the dose amount or frequency of antisense compound is maintained or reduced following an indication that administration of the antisense compound is effective. In certain embodiments, the dose of antisense compound is increased following an indication that administration of the antisense compound is not effective. In certain embodiments, frequency of administration of antisense compound is reduced following an indication that administration of the antisense compound is effective. In certain embodiments, frequency of administration of antisense compound is increased following an indication that administration of the antisense compound is not effective.

In certain embodiments, the methods comprise co-administration of the antisense compound and at least one other therapy. In certain embodiments, an antisense compound and at least one other therapy are co-administered at the same time. In certain embodiments, an antisense compound is administered prior to administration of the at least one other therapy. In certain embodiments, an antisense compound is administered after administration of the at least one other therapy. In certain embodiments, the at least one other therapy comprises administration of one or more of valproic acid, riluzole, hydroxyurea, and a butyrate. In certain embodiments, at least one other therapy comprises administration of trichostatin-A. In certain embodiments, the at least one other therapy comprises administration of stem cells. In certain embodiments, at least one other therapy is gene therapy. In certain embodiments, gene therapy is administered to the CSF and an antisense compound is administered systemically. In certain embodiments, gene therapy is administered to the CSF and an antisense compound is administered systemically and to the CSF. In certain embodiments, the invention provides treatment regimens where initially, an antisense compound is administered to the CSF and systemically, followed by gene therapy administration to the CSF and systemic administration of antisense compound. In certain such embodiments, the subject is an infant at the time of initial treatment. In certain such embodiments, the subject is less that 2 years old. In certain embodiments, antisense compound is administered to the CNS of a subject until the subject is old enough for gene therapy. In certain such embodiments, antisense compound is administered systemically throughout.

In certain embodiments, the antisense compound is administered at a concentration of about 0.01 mg/ml, about 0.05 mg/ml, about 0.1 mg/ml, about 0.5 mg/ml, about 1 mg/ml, about 5 mg/ml, about 10 mg/ml, about 50 mg/ml, or about 100 mg/ml.

In certain embodiments, inclusion of exon 7 of SMN2 mRNA in a motoneuron in the subject is increased. In certain embodiments, inclusion of exon 7 amino acids in SMN2 polypeptide in a motoneuron in the subject is increased.

In certain embodiments, the invention provides methods of increasing inclusion of exon 7 of SMN2 mRNA in a motoneuron in a subject comprising administering to the subject an antisense compound comprising an antisense oligonucleotide complementary to intron 7 of a nucleic acid encoding human SMN2 and thereby increasing inclusion of exon 7 of SMN2 mRNA in the motoneuron in the subject.

In certain embodiments, the invention provides methods of increasing inclusion of exon 7 amino acids in SMN2 polypeptide in a motoneuron in a subject comprising administering to the subject an antisense compound comprising an antisense oligonucleotide complementary to intron 7 of a nucleic acid encoding human SMN2 and thereby increasing inclusion of exon 7 amino acids in SMN2 polypeptide in the motoneuron in the subject.

In certain embodiments, the subject has SMA. In certain embodiments, the subject has type I SMA. In certain embodiments, the subject has type II SMA. In certain embodiments, the subject has type III SMA.

In certain embodiments, a first dose is administered in utero. In certain embodiments, the first dose is administered prior to complete formation of the blood-brain-barrier. In certain embodiments, a first dose is administered within 1 week of birth of the subject. In certain embodiments, a first dose is administered within 1 month of birth of the subject. In certain embodiments, a first dose is administered within 3 months of birth of the subject. In certain embodiments, a first dose is administered within 6 months of birth of the subject. In certain embodiments, a first dose is administered when the subject is from 1 to 2 years of age. In certain embodiments, a first dose is administered when the subject is from 1 to 15 years of age. In certain embodiments, a first dose is administered when the subject is older than 15 years of age.

In certain embodiments, the subject is a mammal. In certain embodiments, the subject is a human.

In certain embodiments, the methods comprise identifying a subject having SMA. In certain embodiments, the subject is identified by measuring electrical activity of one or more muscles of the subject. In certain embodiments, the subject is identified by a genetic test to determine whether the subject has a mutation in the subject's SMN1 gene. In certain embodiments, the subject is identified by muscle biopsy.

In certain embodiments, administering the antisense compound results in an increase in the amount of SMN2 mRNA having exon 7 of at least 10%. In certain embodiments, the increase in the amount of SMN2 mRNA having exon 7 is at least 20%. In certain embodiments, the increase in the amount of SMN2 mRNA having exon 7 is at least 50%. In certain embodiments, the amount of SMN2 mRNA having exon 7 is at least 70%.

In certain embodiments, administering of the antisense compound results in an increase in the amount of SMN2 polypeptide having exon 7 amino acids of at least 10%. In certain embodiments, wherein the increase in the amount of SMN2 polypeptide having exon 7 amino acids is at least 20%. In certain embodiments, the increase in the amount of SMN2 polypeptide having exon 7 amino acids is at least 50%. In certain embodiments, the increase in the amount of SMN2 polypeptide having exon 7 amino acids is at least 70%.

In certain embodiments, the administering of the antisense compound ameliorates at least one symptom of SMA in the subject. In certain embodiments, the administering of the antisense compound results in improved motor function in the subject. In certain embodiments, the administering of the antisense compound results in delayed or reduced loss of motor function in the subject. In certain embodiments, administering of the antisense compound results in improved respiratory function. In certain embodiments, the administering of the antisense compound results in improved survival.

In certain embodiments, at least one nucleoside of the antisense oligonucleotide comprises a modified sugar moiety. In certain embodiments, at least one modified sugar moiety comprises a 2'-methoxyethyl sugar moiety. In certain embodiments, essentially each nucleoside of the antisense oligonucleotide comprises a modified sugar moiety. In certain embodiments, the nucleosides comprising a modified sugar moiety all comprise the same sugar modification. In certain embodiments, wherein each modified sugar moiety comprises a 2'-methoxyethyl sugar moiety. In certain embodiments, each nucleoside of the antisense oligonucleotide comprises a modified sugar moiety. In certain embodiments, the nucleosides all comprise the same sugar modification. In certain embodiments, each modified sugar moiety comprises a 2'-methoxyethyl sugar moiety. In certain embodiments, at least one internucleoside linkage is a phosphorothioate internucleoside linkage. In certain embodiments, each internucleoside linkage is a phosphorothioate internucleoside linkage.

In certain embodiments, the antisense oligonucleotide consists of 10 to 25 linked nucleosides. In certain embodiments, the antisense oligonucleotide consists of 12 to 22 linked nucleosides. In certain embodiments, the antisense oligonucleotide consists of 15 to 20 linked nucleosides. In certain embodiments, the antisense oligonucleotide consists of 18 linked nucleosides.

In certain embodiments, the antisense oligonucleotide is at least 90% complementary to the nucleic acid encoding human SMN2. In certain embodiments, the antisense oligonucleotide is fully complementary to the nucleic acid encoding human SMN2. In certain embodiments, the oligonucleotide has a nucleobase sequence comprising at least 10 contiguous nucleobases of the nucleobase sequence SEQ ID NO: 1. In certain embodiments, the oligonucleotide has a nucleobase sequence comprising at least 15 contiguous nucleobases of the nucleobase sequence SEQ ID NO: 1. In certain embodiments, the oligonucleotide has a nucleobase sequence comprising the nucleobase sequence SEQ ID NO: 1. In certain embodiments, the oligonucleotide has a nucleobase sequence consisting of the nucleobase sequence SEQ ID NO: 1.

In certain embodiments, the antisense compound comprises a conjugate group or terminal group.

In certain embodiments, the antisense compound consists of the antisense oligonucleotide.

In certain embodiments, the antisense compound is also administered systemically. In certain embodiments, the systemic administration is by intravenous or intraperitoneal injection. In certain embodiments, systemic administration and the administration into the central nervous system are performed at the same time. In certain embodiments, systemic administration and the administration into the central nervous system are performed at different times.

In certain embodiments, the invention provides systemic administration of antisense compounds, either alone or in combination with delivery into the CSF. In certain embodiments, pharmaceutical compositions are administered systemically. In certain embodiments, pharmaceutical compositions are administered subcutaneously. In certain embodiments, pharmaceutical compositions are administered intravenously. In certain embodiments, pharmaceutical compositions are administered by intramuscular injection.

In certain embodiments, pharmaceutical compositions are administered both directly to the CSF (e.g., IT and/or ICV injection and/or infusion) and systemically.

In certain embodiments, the invention provides methods of administering to a subject having at least one symptom associated with SMA, at least one dose of an antisense compound comprising an oligonucleotide consisting of 15 to 20 linked nucleosides and having a nucleobase sequence which is 100% complementary to SEQ ID NO. 7 over its entire length, and wherein each nucleoside is a 2'-MOE modified nucleoside; and wherein at least one dose is between 0.1 mg/kg and 5 mg/kg administered to the CSF. In certain such embodiments, the dose is between 0.5 mg/kg and 2 mg/kg. In certain embodiments, at least one dose is administered by bolus injection. In certain such embodiments, the dose is administered by bolus intrathecal injection. In certain embodiments, at least one second dose is administered. In certain such embodiments, the second dose is administered at least 2 weeks after the first dose. In certain embodiments, the second dose is administered at least 4 weeks after the first dose. In certain embodiments, the second dose is administered at least 8 weeks after the first dose. In certain embodiments, the second dose is administered at least 12 weeks after the first dose. In certain embodiments, the second dose is administered at least 16 weeks after the first dose. In certain embodiments, the second dose is administered at least 20 weeks after the first dose. In certain embodiments, the subject is under 2 years old at the time of the first dose. In certain embodiments, the subject is between 2 and 15 years old. In certain embodiments, the subject is between 15 and 30 years old. In certain embodiments, the subject is older than 30 years old. In certain embodiments, at least one symptom associated with SMA is reduced its progression has slowed. In certain embodiments, the oligonucleotide is ISIS396443.

In certain embodiments, the invention provides methods of administering to a subject having at least one symptom associated with SMA, at least one dose of an antisense compound comprising an oligonucleotide consisting of 15 to 20 linked nucleosides and having a nucleobase sequence comprising which is 100% complementary to SEQ ID NO. 7 over its entire length, and wherein each nucleoside is a 2'-MOE modified nucleoside; and wherein at least one dose is administered systemically. In certain such embodiments, at least one dose is administered by bolus injection. In certain such embodiments, the dose is administered by bolus subcutaneous injection. In certain embodiments, the dose administered is between 0.5 mg/kg and 50 mg/kg. In certain embodiments, the dose is between 1 mg/kg and 10 mg/kg. In certain embodiments, the dose is between 1 mg/kg and 5 mg/kg. In certain embodiments, the dose is between 0.5 mg/kg and 1 mg/kg. In certain embodiments, at least one second dose is administered. In certain such embodiments, the second dose is administered at least 2 weeks after the first dose. In certain embodiments, the second dose is administered at least 4 weeks after the first dose. In certain embodiments, the second dose is administered at least 8 weeks after the first dose. In certain embodiments, the second dose is administered at least 12 weeks after the first dose. In certain embodiments, the second dose is administered at least 16 weeks after the first dose. In certain embodiments, the second dose is administered at least 20 weeks after the first dose. In certain embodiments, the subject is under 2 years old at the time of the first dose. In certain embodiments, the subject is between 2 and 15 years old. In certain embodiments, the subject is between 15 and 30 years old. In certain embodiments, the subject is older than 30 years old. In certain embodiments, at least one symptom associated with SMA is reduced its progression has slowed. In certain embodiments, the oligonucleotide is ISIS396443.

In certain embodiments, the invention provides methods of administering to a subject having at least one symptom associated with SMA, at least one dose to the CSF and at least one systemic dose of an antisense compound comprising an oligonucleotide consisting of 15 to 20 linked nucleosides and having a nucleobase sequence which is 100% complementary to SEQ ID NO. 7 over its entire length, and wherein each nucleoside is a 2'-MOE modified nucleoside. In certain such embodiments, the CSF dose is between 0.1 mg/kg and 5 mg/kg. In certain embodiments, the systemic dose is between 0.5 mg/kg and 50 mg/kg. In certain embodiments, at least one CSF dose is administered by bolus injection. In certain such embodiments, at least one CSF dose is administered by bolus intrathecal injection. In certain embodiments, at least one systemic dose is administered by bolus injection. In certain such embodiments, at least one systemic dose is administered by subcutaneous injection. In certain embodiments, the CSF dose and the systemic dose are administered at the same time. In certain embodiments, the CSF dose and the systemic dose are administered at different times. In certain embodiments, the subject is under 2 years old at the time of the first dose. In certain embodiments, the subject is between 2 and 15 years old. In certain embodiments, the subject is between 15 and 30 years old. In certain embodiments, the subject is older than 30 years old. In certain embodiments, at least one symptom associated with SMA is reduced its progression has slowed. In certain embodiments, the oligonucleotide is ISIS396443.

In certain embodiments, the invention provides methods of administering to a subject having at least one symptom associated with SMA, at least one systemic dose of an antisense compound comprising an oligonucleotide consisting of 15 to 20 linked nucleosides and having a nucleobase sequence which is 100% complementary to SEQ ID NO. 7 over its entire length, and wherein each nucleoside is a 2'-MOE modified nucleoside; and at least one dose of a gene therapy agent. In certain embodiments, the systemic dose is between 0.5 mg/kg and 50 mg/kg. In certain embodiments, at least one systemic dose is administered by bolus injection. In certain such embodiments, at least one systemic dose is administered by subcutaneous injection. In certain embodiments, the systemic dose and the gene therapy agent are administered at the same time. In certain embodiments, the systemic dose and the gene therapy agent are administered at different times. In certain embodiments, the gene therapy agent is administered to the CSF. In certain such embodiments, the gene therapy agent is administered by intrathecal injection and/or infusion. In certain such embodiments, the gene therapy agent is administered by intracerebroventricular injection and/or infusion. In certain embodiments, the subject is under 2 years old at the time of the first dose. In certain embodiments, the subject is between 2 and 15 years old. In certain embodiments, the subject is between 15 and 30 years old. In certain embodiments, the subject is older than 30 years old. In certain embodiments, at least one symptom associated with SMA is reduced or its progression has slowed. In certain embodiments, the oligonucleotide is ISIS396443.

In certain embodiments, the invention provides methods of selecting a subject having at least one symptom associated with SMA and administering an antisense compound according to any of the methods above. In certain such embodiments, at least one symptom of SMA is assessed after administration. In certain such embodiments, at least one symptom of SMA is improved. In certain such embodiments, at least one symptom of SMA does not progress or progresses more slowly compared to a subject who has not received administration of antisense compound.

In certain embodiments, the invention provides an antisense compound comprising an antisense oligonucleotide complementary to intron 7 of a nucleic acid encoding human SMN2, for use in any of the above methods. In certain embodiments, the invention provides such a compound for use in treating a disease or condition associated with survival motor neuron 1 (SMN1).

In certain embodiments, the invention provides use of an antisense compound comprising an antisense oligonucleotide complementary to intron 7 of a nucleic acid encoding human SMN2 in the manufacture of a medicament for use in any of the above methods. In certain embodiments, the medicament is for treating a disease or condition associated with survival motor neuron 1 (SMN1).

BRIEF DESCRIPTION OF THE FIGURES

FIG. 3A shows the first such experiment and FIG. 3B shows a repeated experiment testing a different concentration of antisense compound, as noted and including data for normal mice for comparison.

DETAILED DESCRIPTION OF THE INVENTION

Figure 1:
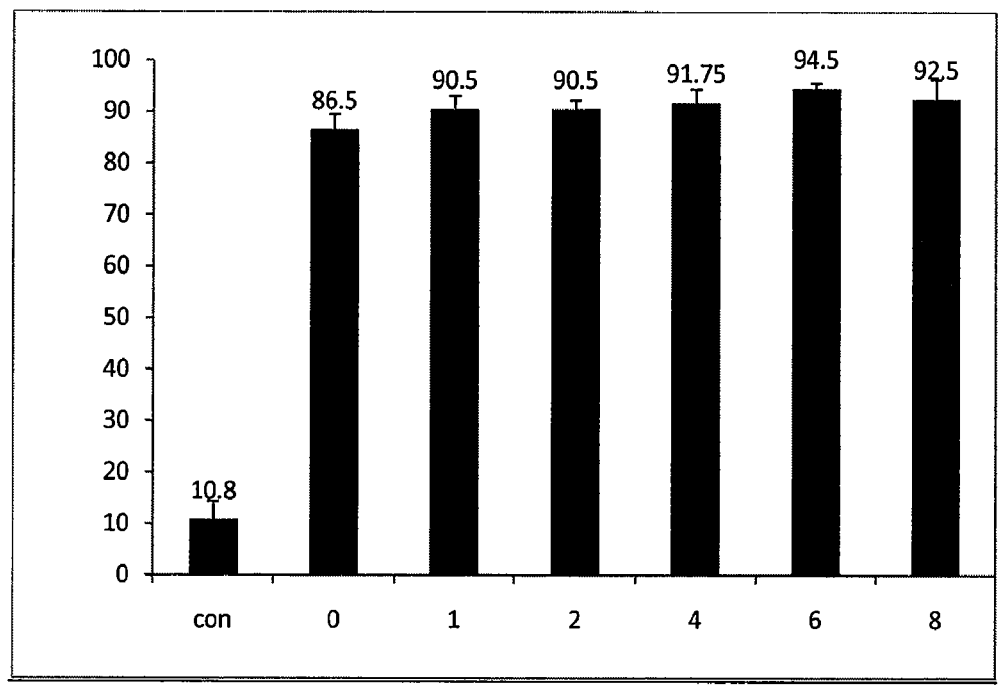
FIG. 1 shows results from a duration of action study discussed in Example 4, in which the percent of SMN2 that includes exon 7 (y-axis) was assessed at 0, 2, 4, 6, and 8 weeks after termination of 7 days of treatment (x-axis). The week "0" sample was taken 1 day after termination of treatment. CON represents saline treated mice. There was no difference in % inclusion among control saline treated mice at different time points from 0 to 6 months.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

I. Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

"Nucleoside" means a compound comprising a heterocyclic base moiety and a sugar moiety. Nucleosides include, but are not limited to, naturally occurring nucleosides, modified nucleosides, and nucleosides having mimetic bases and/or sugar groups. Nucleosides may be modified with any of a variety of substituents.

"Sugar moiety" means a natural or modified sugar or sugar surrogate.

"Natural sugar" means a ribofuranose moiety of DNA (2'-H) or RNA (2'-OH).

"Modified sugar" means a ribofuranose moiety comprising at least one substituent other than that of a natural sugar.

"Sugar surrogate" means a structure other than a ribofuranose ring which is capable of substituting for the sugar of a nucleoside. Examples of sugar surrogates include, but are not limited to, open ring systems, 6-membered rings, sugars in which the oxygen is replace with, for example, sulfur or nitrogen. For example, sugar surrogates include, but are not limited to morpholinos and 4'-thio-containing sugars.

"Nucleobase" means the heterocyclic base portion of a nucleoside. Nucleobases may be naturally occurring or may be modified. In certain embodiments, a nucleobase may comprise any atom or group of atoms capable of hydrogen bonding to a nucleobase of another nucleic acid.

"Nucleotide" means a nucleoside comprising a phosphate linking group. As used herein, nucleosides include nucleotides.

"Modified nucleoside" a nucleoside comprising at least one modification compared to naturally occurring RNA or DNA nucleosides. Such modification may be at the sugar moiety and/or at the nucleobase.

"Bicyclic nucleoside" or "BNA" means a nucleoside wherein the sugar moiety of the nucleoside comprises a bridge connecting two carbon atoms of the sugar ring, thereby forming a bicyclic sugar moiety.

"4'-2' bicyclic nucleoside" means a bicyclic nucleoside comprising a furanose ring comprising a bridge connecting two carbon atoms of the furanose ring connects the 2' carbon atom and the 4' carbon atom of the sugar ring.

"2'-modified" or "2'-substituted" means a nucleoside comprising a sugar comprising a substituent at the 2' position other than H or OH.

"2'-OMe" or "2'-OCH$_3$" or "2'-O-methyl" each means a nucleoside comprising a sugar comprising an —OCH$_3$ group at the 2' position of the sugar ring.

"MOE" or "2'-MOE" or "2'-OCH$_2$CH$_2$OCH$_3$" or "2'-O-methoxyethyl" each means a nucleoside comprising a sugar comprising a —OCH$_2$CH$_2$OCH$_3$ group at the 2' position of the sugar ring.

"Oligonucleotide" means a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

"Oligonucleoside" means an oligonucleotide in which none of the internucleoside linkages contains a phosphorus atom. As used herein, oligonucleotides include oligonucleosides.

"Modified oligonucleotide" means an oligonucleotide comprising at least one modified nucleoside and/or at least one modified internucleoside linkage.

"Internucleoside linkage" means a covalent linkage between adjacent nucleosides of an oligonucleotide.

"Naturally occurring internucleoside linkage" means a 3' to 5' phosphodiester linkage.

"Modified internucleoside linkage" means any internucleoside linkage other than a naturally occurring internucleoside linkage.

"Oligomeric compound" means a compound comprising an oligonucleotide. In certain embodiments, an oligomeric compound consists of an oligonucleotide. In certain embodiments, an oligomeric compound further comprises one or more conjugate and/or terminal groups.

"Antisense compound" means an oligomeric compound, at least a portion of which is at least partially complementary to a target nucleic acid to which it hybridizes, wherein such hybridization results at least one antisense activity.

"Antisense oligonucleotide" means an antisense compound wherein the oligomeric compound consists of an oligonucleotide.

"Antisense activity" refers to any detectable and/or measurable effect attributable to the hybridization of an antisense compound to its target nucleic acid. In certain embodiments, such antisense activity is an increase or decrease in an amount of a nucleic acid or protein. In certain embodiments, such antisense activity is a change in the ratio of splice variants of a nucleic acid or protein. In certain embodiments, such antisense activity is a phenotypic change in a cell and/or subject.

"Detecting" or "measuring" of antisense activity may be direct or indirect. For example, in certain embodiments, antisense activity is assessed by detecting and/or measuring the amount of target nucleic acid or protein or the relative amounts of splice variants of a target nucleic acid or protein. In certain embodiments, antisense activity is detected by observing a phenotypic change in a cell or animal. In connection with any activity, response, or effect, the terms "detecting" and "measuring," indicate that a test for detecting or measuring is performed. Such detection and/or measuring may include values of zero. Thus, if a test for detection or measuring results in a finding of no activity (activity of zero), the step of detecting or measuring the activity has nevertheless been performed.

"Target nucleic acid" refers to any nucleic acid molecule the expression, amount, or activity of which is capable of being modulated by an antisense compound.

"Target mRNA" means a pre-selected RNA molecule that encodes a protein.

"Target pre-mRNA" means a pre-selected RNA transcript that has not been fully processed into mRNA. Notably, pre-mRNA includes one or more intron.

"Target protein" means a protein encoded by a target nucleic acid.

"Modulation" means to a perturbation of function or activity. In certain embodiments, modulation means an increase in gene expression. In certain embodiments, modulation means a decrease in gene expression.

"Expression" means any functions and steps by which a gene's coded information is converted into structures present and operating in a cell.

"Nucleobase sequence" means the order of contiguous nucleobases, in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that a first nucleic acid is capable of hybridizing to a second nucleic acid under stringent hybridization conditions. For example, an antisense compound is complementary to its target nucleic acid if it is capable of hybridizing to the target nucleic acid under stringent hybridization conditions.

"Fully complementary" means each nucleobase of a first nucleic acid is capable of pairing with a nucleobase at each corresponding contiguous position in a second nucleic acid.

"Percent complementarity" of an antisense compound means the percentage of nucleobases of the antisense compound that are complementary to an equal-length portion of a target nucleic acid. Percent complementarity is calculated by dividing the number of nucleobases of the antisense oligonucleotide that are complementary to nucleobases at corresponding contiguous positions in the target nucleic acid by the total length of the antisense compound.

"Percent identity" means the number of nucleobases in first nucleic acid that are identical to nucleobases at corresponding positions in a second nucleic acid, divided by the total number of nucleobases in the first nucleic acid.

"Hybridize" means the annealing of complementary nucleic acids that occurs through nucleobase complementarity.

"Mismatch" means a nucleobase of a first nucleic acid that is not capable of pairing with a nucleobase at a corresponding position of a second nucleic acid.

"Identical nucleobase sequence" means having the same nucleobase sequence, independent of any chemical modifications to the nucleosides.

"Different modifications" or "differently modified" refer to nucleosides or internucleoside linkages that have different nucleoside modifications or internucleoside linkages than one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified, unless otherwise indicated. For example, a nucleoside comprising a 2'-OMe modified sugar and an adenine nucleobase and a nucleoside comprising a 2'-OMe modified sugar and a thymine nucleobase are not differently modified.

"The same modifications" refer to nucleosides and internucleoside linkages (including unmodified nucleosides and internucleoside linkages) that are the same as one another. Thus, for example, two unmodified DNA nucleoside have "the same modification," even though the DNA nucleoside is unmodified.

"Type of modification" or nucleoside of a "type" means the modification of a nucleoside and includes modified and unmodified nucleosides. Accordingly, unless otherwise indicated, a "nucleoside having a modification of a first type" may be an unmodified nucleoside.

"Separate regions" of an oligonucleotide means a portion of an oligonucleotide wherein the nucleosides and internucleoside linkages within the region all comprise the same modifications; and the nucleosides and/or the internucleoside linkages of any neighboring portions include at least one different modification.

"Motif" means a pattern of modified and/or unmodified nucleobases, sugars, and/or internucleoside linkages in an oligonucleotide.

"Fully modified oligonucleotide" means each nucleobase, each sugar, and/or each internucleoside linkage is modified.

"Uniformly modified oligonucleotide" means each nucleobase, each sugar, and/or each internucleoside linkage has the same modification throughout the modified oligonucleotide.

"Alternating motif" means an oligonucleotide or a portion thereof, having at least four separate regions of modified nucleosides in a pattern $(AB)_n A_m$ where A represents a region of nucleosides having a first type of modification; B represent a region of nucleosides having a different type of modification; n is 2-15; and m is 0 or 1. Thus, in certain embodiments, alternating motifs include 4, 5, 6, 7, 8, 9, 10, 11, 12, 13, 14, 15, 16, 17, 18, 19, or 20 or more alternating regions. In certain embodiments, each A region and each B region independently comprises 1-4 nucleosides.

"Subject" means a human or non-human animal selected for treatment or therapy.

"Subject in need thereof" means a subject identified as in need of a therapy or treatment. In such embodiments, a subject has one or more indications of having or developing SMA.

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, or intramuscular administration.

"Systemic administration" means administration to an area other than the intended locus of activity. Examples or systemic administration are subcutaneous administration and intravenous administration, and intraperitoneal administration.

"Subcutaneous administration" means administration just below the skin.

"Intravenous administration" means administration into a vein.

"Cerebrospinal fluid" or "CSF" means the fluid filling the space around the brain and spinal cord.

"Administration into the cerebrospinal fluid" means any administration that delivers a substance directly into the CSF.

"Intracerebroventricular" or "ICV" mean administration into the ventricular system of the brain.

"Intrathecal" or "IT" means administration into the CSF under the arachnoid membrane which covers the brain and spinal cord. IT injection is performed through the theca of the spinal cord into the subarachnoid space, where a pharmaceutical agent is injected into the sheath surrounding the spinal cord.

"Induction phase" means a dosing phase during which administration is initiated and steady state concentrations of active pharmaceutical agent are achieved in a target tissue. For example, an induction phase is a dosing phase during which steady state concentrations of antisense oligonucleotide are achieved in liver.

"Maintenance phase" means a dosing phase after target tissue steady state concentrations of drug have been achieved.

"Duration" means the period of time during which an activity or event continues. For example, the duration of an induction phase is the period of time during which induction doses are administered.

"Maintenance dose" means a dose administered at a single administration during the maintenance phase. As used herein, "induction dose" means a dose administered at a single administration during the induction phase.

"Co-administration" means administration of two or more pharmaceutical agents to a subject. The two or more pharmaceutical agents may be in a single pharmaceutical composition, or may be in separate pharmaceutical compositions. Each of the two or more pharmaceutical agents may be administered through the same or different routes of administration. Co-administration encompasses administration in parallel or sequentially.

"Therapy" means a disease treatment method. In certain embodiments, therapy includes, but is not limited to surgical therapies, chemical therapies, and physical interventions, such as assisted respiration, feeding tubes, and physical therapy for the purpose of increasing strength.

"Treatment" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Prevent the onset of" means to prevent the development a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition.

"Slow the progression of" means that the severity of at least one symptom associated with a disease or condition worsens less quickly.

"Exon 7 amino acids" means the portion of an SMN protein that correspond to exon 7 of the SMN RNA. Exon 7 amino acids are present in SMN protein expressed from SMN RNA where exon 7 was not excluded during splicing.

"SMN protein" means normal full length survival motor neuron protein. SMN may be expressed from either an SMN1 gene or from an SMN2 gene, provided that exon 7 is present in the mature mRNA and the exon 7 amino acids are present in the SMN protein.

"Dose" means a specified quantity of a pharmaceutical agent provided in a single administration or over a specified amount of time. In certain embodiments, a dose may be administered in two or more boluses, tablets, or injections. For example, in certain embodiments, where subcutaneous or inrathecal or ICV administration is desired, the desired dose requires a volume not easily accommodated by a single injection. In such embodiments, two or more injections may be used to achieve the desired dose. In the setting of continuous infusion, dose may be expressed as the quantity of a pharmaceutical agent delivered per unit of time.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Therapeutically effective amount" means an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a modified oligonucleotide and a sterile aqueous solution.

"Acceptable safety profile" means a pattern of side effects that is within clinically acceptable limits.

"Side effect" means a physiological response attributable to a treatment other than desired effects.

1. Certain Modified Oligonucleotides

In certain embodiments, the present invention provides methods and compositions involving antisense oligonucleotides comprising one or more modification compared to oligonucleotides of naturally occurring oligomers, such as DNA or RNA. Such modified antisense oligonucleotides may possess one or more desirable properties. Certain such modifications alter the antisense activity of the antisense oligonucleotide, for example by increasing affinity of the antisense oligonucleotide for its target nucleic acid, increasing its resistance to one or more nucleases, and/or altering the pharmacokinetics or tissue distribution of the oligonucleotide. In certain embodiments, such modified antisense oligonucleotides comprise one or more modified nucleosides and/or one or more modified nucleoside linkages and/or one or more conjugate groups.

a. Certain Modified Nucleosides

In certain embodiments, antisense oligonucleotides comprise one or more modified nucleosides. Such modified nucleosides may include a modified sugar and/or a modified nucleobase. In certain embodiments, incorporation of such modified nucleosides in an oligonucleotide results in increased affinity for a target nucleic acid and/or increased stability, including but not limited to, increased resistance to nuclease degradation, and or improved toxicity and/or uptake properties of the modified oligonucleotide.

i. Certain Nucleobases

The naturally occurring base portion of nucleosides are heterocyclic base, typically purines and pyrimidines. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to incorporation into the compounds described herein. In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

ii. Certain Modified Sugars and Sugar Surrogates

Antisense oligonucleotides of the present invention can optionally contain one or more nucleosides wherein the sugar moiety is modified, compared to a natural sugar. Oligonucleotides comprising such sugar modified nucleosides may have enhanced nuclease stability, increased binding affinity or some other beneficial biological property. Such modifications include without limitation, addition of substituent groups, bridging of non-geminal ring atoms to form a bicyclic nucleic acid (BNA), replacement of the ribosyl ring oxygen atom with S, N(R), or $C(R_1)(R)_2$ (R=H, $C_1$-$C_{12}$ alkyl or a protecting group) and combinations of these such as for example a 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $O(CH_2)_2SCH_3$, $O(CH_2)_2$—O—$N(R_m)(R_n)$, and O—$CH_2$—C(=O)—$N(R_m)(R_n)$, where each $R_m$ and $R_n$ is, independently, H or substituted or unsubstituted $C_1$-$C_{10}$ alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-β-D-($CH_2$)—O-2' (β-D-LNA); 4'-($CH_2$)—S-2; 4'-α-L-($CH_2$)—O-2' (α-L-LNA); 4'-($CH_2$)$_2$—O-2' (ENA); 4'-C($CH_3$)$_2$—O-2' (see PCT/US2008/068922); 4'-CH($CH_3$)—O-2' and 4'-C—H($CH_2OCH_3$)—O-2' (see U.S. Pat. No. 7,399,845, issued on Jul. 15, 2008); 4'-$CH_2$—N($OCH_3$)-2' (see PCT/US2008/064591); 4'-$CH_2$—O—N($CH_3$)-2' (see published U.S. Patent Application US2004-0171570, published Sep. 2, 2004); 4'-$CH_2$—N(R)—O-2' (see U.S. Pat. No. 7,427,672, issued on Sep. 23, 2008); 4'-$CH_2$—C($CH_3$)-2' and 4'-$CH_2$—C(=$CH_2$)-2' (see PCT/US2008/066154); and wherein R is, independently, H, $C_1$-$C_{12}$ alkyl, or a protecting group.

In certain embodiments, the present invention provides modified nucleosides comprising modified sugar moieties that are not bicyclic sugar moieties. Certain such modified nucleosides are known. In certain embodiments, the sugar ring of a nucleoside may be modified at any position. Examples of sugar modifications useful in this invention include, but are not limited to compounds comprising a sugar substituent group selected from: OH, F, O-alkyl, S-alkyl, N-alkyl, or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In certain such embodiments, such substituents are at the 2' position of the sugar.

In certain embodiments, modified nucleosides comprise a substituent at the 2' position of the sugar. In certain embodiments, such substituents are selected from among: a halide (including, but not limited to F), allyl, amino, azido, thio, O-allyl, O—$C_1$-$C_{10}$ alkyl, —$OCF_3$, O—$(CH_2)_2$—O—$CH_3$, 2'-$O(CH_2)_2SCH_3$, O—$(CH_2)_2$—O—$N(R_m)(R_n)$, or O—CH2-C(=O)—$N(R_m)(R_n)$, where each $R_m$ and $R_n$ is, independently, H or substituted or unsubstituted $C_1$-$C_{10}$ alkyl.

In certain embodiments, modified nucleosides suitable for use in the present invention are: 2-methoxyethoxy, 2'-O-methyl (2'-O—$CH_3$), 2'-fluoro (2'-F).

In certain embodiments, modified nucleosides having a substituent group at the 2'-position selected from: $O[(CH_2)_nO]_mCH_3$, $O(CH_2)_nNH_2$, $O(CH_2)_nCH_3$, $O(CH_2)_nONH_2$, $OCH_2C(=O)N(H)CH_3$, and $O(CH_2)_nON[CH_2)_nCH_3]_2$, where n and m are from 1 to about 10. Other 2'-sugar substituent groups include: $C_1$ to $C_{10}$ alkyl, substituted alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an oligomeric compound, and other substituents having similar properties.

In certain embodiments, modified nucleosides comprise a 2'-MOE side chain (Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

In certain embodiments, 2'-sugar substituent groups are in either the arabino (up) position or ribo (down) position. In certain such embodiments, a 2'-arabino modification is 2'-F arabino (FANA). Similar modifications can also be made at other positions on the sugar, particularly the 3' position of the sugar on a 3' terminal nucleoside or in 2'-5' linked oligonucleotides and the 5' position of 5' terminal nucleotide.

In certain embodiments, nucleosides suitable for use in the present invention have sugar surrogates such as cyclobutyl in place of the ribofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

In certain embodiments, the present invention provides nucleosides comprising a modification at the 2'-position of the sugar. In certain embodiments, the invention provides nucleosides comprising a modification at the 5'-position of the sugar. In certain embodiments, the invention provides nucleosides comprising modifications at the 2'-position and the 5'-position of the sugar. In certain embodiments, modified nucleosides may be useful for incorporation into oligonucleotides. In certain embodiment, modified nucleosides are incorporated into oligonucleotides at the 5'-end of the oligonucleotide.

b. Certain Internucleoside Linkages

Antisense oligonucleotides of the present invention can optionally contain one or more modified internucleoside linkages. The two main classes of linking groups are defined by the presence or absence of a phosphorus atom. Representative phosphorus containing linkages include, but are not limited to, phosphodiesters (P=O), phosphotriesters, methylphosphonates, phosphoramidate, and phosphorothioates (P=S). Representative non-phosphorus containing linking groups include, but are not limited to, methylenemethylimino (—CH2-N(CH3)-O—CH2-), thiodiester (—O—C(O)—S—), thionocarbamate (—O—C(O)(NH)—S—); siloxane (—O—Si(H)2-O—); and N,N'-dimethylhydrazine (—CH2-N(CH3)-N(CH3)-). Oligonucleotides having non-phosphorus linking groups are referred to as oligonucleosides. Modified linkages, compared to natural phosphodiester linkages, can be used to alter, typically increase, nuclease resistance of the oligonucleotides. In certain embodiments, linkages having a chiral atom can be prepared as racemic mixtures, as separate enantomers. Representative chiral linkages include, but are not limited to, alkylphosphonates and phosphorothioates. Methods of preparation of phosphorous-containing and non-phosphorous-containing linkages are well known to those skilled in the art.

The antisense oligonucleotides described herein contain one or more asymmetric centers and thus give rise to enantiomers, diastereomers, and other stereoisomeric configurations that may be defined, in terms of absolute stereochemistry, as (R) or (S), such as for sugar anomers, or as (D) or (L) such as for amino acids et al. Included in the antisense compounds provided herein are all such possible isomers, as well as their racemic and optically pure forms.

In certain embodiments, antisense oligonucleotides have at least one modified internucleoside linkage. In certain embodiments, antisense oligonucleotides have at least 2 modified internucleoside linkages. In certain embodiments, antisense oligonucleotides have at least 3 modified internucleoside linkages. In certain embodiments, antisense oligonucleotides have at least 10 modified internucleoside linkages. In certain embodiments, each internucleoside linkage of an antisense oligonucleotide is a modified internucleoside linkage. In certain embodiments, such modified internucleoside linkages are phosphorothioate linkages.

c. Lengths

In certain embodiments, the present invention provides antisense oligonucleotides of any of a variety of ranges of lengths. In certain embodiments, the invention provides antisense compounds or antisense oligonucleotides comprising or consisting of X-Y linked nucleosides, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides antisense compounds or antisense oligonucleotides comprising or consisting of: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked nucleosides.

In certain embodiments, antisense compounds or antisense oligonucleotides of the present invention are 15 nucleosides in length. In certain embodiments, antisense compounds or antisense oligonucleotides of the present invention are 16 nucleosides in length. In certain embodiments, antisense compounds or antisense oligonucleotides of the present invention are 17 nucleosides in length. In certain embodiments, antisense compounds or antisense oligonucleotides of the present invention are 18 nucleosides in length. In certain embodiments, antisense compounds or antisense oligonucleotides of the present invention are 19 nucleosides in length. In certain embodiments, antisense compounds or antisense oligonucleotides of the present invention are 20 nucleosides in length.

d. Certain Oligonucleotide Motifs

In certain embodiments, antisense oligonucleotides have chemically modified subunits arranged in specific orientations along their length. In certain embodiments, antisense oligonucleotides of the invention are fully modified. In certain embodiments, antisense oligonucleotides of the invention are uniformly modified. In certain embodiments, antisense oligonucleotides of the invention are uniformly modified and each nucleoside comprises a 2'-MOE sugar moiety. In certain embodiments, antisense oligonucleotides of the invention are uniformly modified and each nucleoside comprises a 2'-OMe sugar moiety. In certain embodiments, antisense oligonucleotides of the invention are uniformly modified and each nucleoside comprises a morpholino sugar moiety.

In certain embodiments, oligonucleotides of the invention comprise an alternating motif. In certain such embodiments, the alternating modification types are selected from among 2'-MOE, 2'-F, a bicyclic sugar-modified nucleoside, and DNA (unmodified 2'-deoxy). In certain such embodiments, each alternating region comprises a single nucleoside.

In certain embodiments, oligonucleotides of the invention comprise one or more block of nucleosides of a first type and one or more block of nucleosides of a second type.

In certain embodiments, one or more alternating regions in an alternating motif include more than a single nucleoside of a type. For example, oligomeric compounds of the present invention may include one or more regions of any of the following nucleoside motifs:

$Nu_1 Nu_1 Nu_2 Nu_2 Nu_1 Nu_1$;
$Nu_1 Nu_2 Nu_2 Nu_1 Nu_2 Nu_2$;
$Nu_1 Nu_1 Nu_2 Nu_1 Nu_1 Nu_2$;
$Nu_1 Nu_2 Nu_2 Nu_1 Nu_2 Nu_1 Nu_1 Nu_2 Nu_2$;
$Nu_1 Nu_2 Nu_1 Nu_2 Nu_1 Nu_1$;
$Nu_1 Nu_1 Nu_2 Nu_1 Nu_2 Nu_1 Nu_2$;
$Nu_1 Nu_2 Nu_1 Nu_2 Nu_1 Nu_1$;
$Nu_1 Nu_2 Nu_2 Nu_1 Nu_1 Nu_2 Nu_2 Nu_1 Nu_2 Nu_1 Nu_2 Nu_1 Nu_1$;
$Nu_2 Nu_1 Nu_2 Nu_2 Nu_1 Nu_1 Nu_2 Nu_2 Nu_1 Nu_1 Nu_1 Nu_2 Nu_1 Nu_1$; or
$Nu_1 Nu_2 Nu_1 Nu_2 Nu_2 Nu_1 Nu_1 Nu_2 Nu_2 Nu_1 Nu_2 Nu_1 Nu_2 Nu_1 Nu_1$;

wherein $Nu_1$ is a nucleoside of a first type and $Nu_2$ is a nucleoside of a second type. In certain embodiments, one of $Nu_1$ and $Nu_2$ is a 2'-MOE nucleoside and the other of $Nu_1$ and $Nu_2$ is a selected from: a 2'-OMe modified nucleoside, BNA, and an unmodified DNA or RNA nucleoside.

2. Oligomeric Compounds

In certain embodiments, the present invention provides oligomeric compounds. In certain embodiments, oligomeric compounds are comprised only of an oligonucleotide. In certain embodiments, an oligomeric compound comprises an oligonucleotide and one or more conjugate and/or terminal group. Such conjugate and/or terminal groups may be added to oligonucleotides having any of the chemical motifs discussed above. Thus, for example, an oligomeric compound comprising an oligonucleotide having region of alternating nucleosides may comprise a terminal group.

a. Certain Conjugate Groups

In certain embodiments, oligonucleotides of the present invention are modified by attachment of one or more conjugate groups. In general, conjugate groups modify one or more properties of the attached oligomeric compound including but not limited to, pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Lett., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Lett., 1993, 3, 2765-2770), a thiocholesterol (Oberhauser et al., Nucl. Acids Res., 1992, 20, 533-538), an aliphatic chain, e.g., dodecan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130.

Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723;

5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Conjugate groups may be attached to either or both ends of an oligonucleotide (terminal conjugate groups) and/or at any internal position.

b. Terminal Groups

In certain embodiments, oligomeric compounds comprise terminal groups at one or both ends. In certain embodiments, a terminal group may comprise any of the conjugate groups discussed above. In certain embodiments, terminal groups may comprise additional nucleosides and/or inverted abasic nucleosides. In certain embodiments, a terminal group is a stabilizing group.

In certain embodiments, oligomeric compounds comprise one or more terminal stabilizing group that enhances properties such as for example nuclease stability. Included in stabilizing groups are cap structures. The terms "cap structure" or "terminal cap moiety," as used herein, refer to chemical modifications, which can be attached to one or both of the termini of an oligomeric compound. Certain such terminal modifications protect the oligomeric compounds having terminal nucleic acid moieties from exonuclease degradation, and can help in delivery and/or localization within a cell. The cap can be present at the 5'-terminus (5'-cap) or at the 3'-terminus (3'-cap) or can be present on both termini. (for more details see Wincott et al., International PCT publication No. WO 97/26270; Beaucage and Tyer, 1993, Tetrahedron 49, 1925; U.S. Patent Application Publication No. U.S. 2005/0020525; and WO 03/004602.

In certain embodiments, one or more additional nucleosides is added to one or both terminal ends of an oligonucleotide of an oligomeric compound. Such additional terminal nucleosides are referred to herein as terminal-group nucleosides. In a double-stranded compound, such terminal-group nucleosides are terminal (3' and/or 5') overhangs. In the setting of double-stranded antisense compounds, such terminal-group nucleosides may or may not be complementary to a target nucleic acid. In certain embodiments, the terminal group is a non-nucleoside terminal group. Such non-terminal groups may be any terminal group other than a nucleoside.

c. Oligomeric Compound Motifs

In certain embodiments, oligomeric compounds of the present invention comprise a motif:

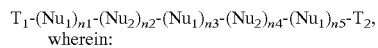

wherein:

$Nu_1$, is a nucleoside of a first type;
$Nu_2$, is a nucleoside of a second type;
each of n1 and n5 is, independently from 0 to 3;
the sum of n2 plus n4 is between 10 and 25;
n3 is from 0 and 5; and
each $T_1$ and $T_2$ is, independently, H, a hydroxyl protecting group, an optionally linked conjugate group or a capping group.

In certain such embodiments, the sum of n2 and n4 is 13 or 14; n1 is 2; n3 is 2 or 3; and n5 is 2. In certain such embodiments, oligomeric compounds of the present invention comprise a motif selected from Table A.

TABLE A

| n1 | n2 | n3 | n4 | n5 |
|----|----|----|----|----|
| 2  | 16 | 0  | 0  | 2  |
| 2  | 2  | 3  | 11 | 2  |
| 2  | 5  | 3  | 8  | 2  |

TABLE A-continued

| n1 | n2 | n3 | n4 | n5 |
|----|----|----|----|----|
| 2  | 8  | 3  | 5  | 2  |
| 2  | 11 | 3  | 2  | 2  |
| 2  | 9  | 3  | 4  | 2  |
| 2  | 10 | 3  | 3  | 2  |
| 2  | 3  | 3  | 10 | 2  |
| 2  | 4  | 3  | 9  | 2  |
| 2  | 6  | 3  | 7  | 2  |
| 2  | 7  | 3  | 6  | 2  |
| 2  | 8  | 6  | 2  | 2  |
| 2  | 2  | 2  | 12 | 2  |
| 2  | 3  | 2  | 11 | 2  |
| 2  | 4  | 2  | 10 | 2  |
| 2  | 5  | 2  | 9  | 2  |
| 2  | 6  | 2  | 8  | 2  |
| 2  | 7  | 2  | 7  | 2  |
| 2  | 8  | 2  | 6  | 2  |
| 2  | 9  | 2  | 5  | 2  |
| 2  | 10 | 2  | 4  | 2  |
| 2  | 11 | 2  | 3  | 2  |
| 2  | 12 | 2  | 2  | 2  |

Table A is intended to illustrate, but not to limit the present invention. The oligomeric compounds depicted in Table A each comprise 20 nucleosides. Oligomeric compounds comprising more or fewer nucleosides can easily by designed by selecting different numbers of nucleosides for one or more of n1-n5. In certain embodiments, $Nu_1$ and $Nu_2$ are each selected from among: 2'-MOE, 2'-OMe, DNA, and a bicyclic nucleoside.

3. Antisense

In certain embodiments, oligomeric compounds of the present invention are antisense compounds. Accordingly, in such embodiments, oligomeric compounds hybridize with a target nucleic acid, resulting in an antisense activity.

a. Hybridization

In certain embodiments, the invention provides antisense compounds that specifically hybridize to a target nucleic acid when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

Thus, "stringent hybridization conditions" or "stringent conditions" means conditions under which an antisense compounds hybridize to a target sequence, but to a minimal number of other sequences. Stringent conditions are sequence-dependent and will be different in different circumstances, and "stringent conditions" under which antisense oligonucleotides hybridize to a target sequence are determined by the nature and composition of the antisense oligonucleotides and the assays in which they are being investigated.

It is understood in the art that incorporation of nucleotide affinity modifications may allow for a greater number of mismatches compared to an unmodified compound. Similarly, certain nucleobase sequences may be more tolerant to mismatches than other nucleobase sequences. One of ordinary skill in the art is capable of determining an appropriate number of mismatches between oligonucleotides, or between an antisense oligonucleotide and a target nucleic acid, such as by determining melting temperature (Tm). Tm or ΔTm can be calculated by techniques that are familiar to one of ordinary skill in the art. For example, techniques described in Freier et al. (Nucleic Acids Research, 1997, 25, 22: 4429-4443) allow b. Pre-mRNA Processing

In certain embodiments, antisense compounds provided herein are complementary to a pre-mRNA. In certain embodiments, such antisense compounds alter splicing of the pre-mRNA. In certain such embodiments, the ratio of one variant of a mature mRNA corresponding to a target pre-mRNA to another variant of that mature mRNA is altered. In certain such embodiments, the ratio of one variant of a protein expressed from the target pre-mRNA to another variant of the protein is altered. Certain oligomeric compounds and nucleobase sequences that may be used to alter splicing of a pre-mRNA may be found for example in U.S. Pat. No. 6,210,892; U.S. Pat. No. 5,627,274; U.S. Pat. Nos. 5,665,593; 5,916,808; U.S. Pat. No. 5,976,879; US2006/0172962; US2007/002390; US2005/0074801; US2007/0105807; US2005/0054836; WO 2007/090073; WO2007/047913, Hua et al., PLoS Biol 5(4):e73; Vickers et al., J. Immunol. 2006 Mar. 15; 176(6): 3652-61; and Hua et al., American J. of Human Genetics (April 2008) 82, 1-15, each of which is hereby incorporated by reference in its entirety for any purpose. In certain embodiments antisense sequences that alter splicing are modified according to motifs of the present invention.

Antisense is an effective means for modulating the expression of one or more specific gene products and is uniquely useful in a number of therapeutic, diagnostic, and research applications. Provided herein are antisense compounds useful for modulating gene expression via antisense mechanisms of action, including antisense mechanisms based on target occupancy. In one aspect, the antisense compounds provided herein modulate splicing of a target gene. Such modulation includes promoting or inhibiting exon inclusion. Further provided herein are antisense compounds targeted to cis splicing regulatory elements present in pre-mRNA molecules, including exonic splicing enhancers, exonic splicing silencers, intronic splicing enhancers and intronic splicing silencers. Disruption of cis splicing regulatory elements is thought to alter splice site selection, which may lead to an alteration in the composition of splice products.

Processing of eukaryotic pre-mRNAs is a complex process that requires a multitude of signals and protein factors to achieve appropriate mRNA splicing. Exon definition by the spliceosome requires more than the canonical splicing signals which define intron-exon boundaries. One such additional signal is provided by cis-acting regulatory enhancer and silencer sequences. Exonic splicing enhancers (ESE), exonic splicing silencers (ESS), intronic splicing enhancers (ISE) and intron splicing silencers (ISS) have been identified which either repress or enhance usage of splice donor sites or splice acceptor sites, depending on their site and mode of action (Yeo et al. 2004, *Proc. Natl. Acad. Sci. U.S.A.* 101(44):15700-15705). Binding of specific proteins (trans factors) to these regulatory sequences directs the splicing process, either promoting or inhibiting usage of particular splice sites and thus modulating the ratio of splicing products (Scamborova et al. 2004, *Mol. Cell. Biol.* 24(5):1855-1869; Hovhannisyan and Carstens, 2005, *Mol. Cell. Biol.* 25(1):250-263; Minovitsky et al. 2005, *Nucleic Acids Res.* 33(2):714-724).

4. Pharmaceutical Compositions

In certain embodiments, the present invention provides pharmaceutical compositions comprising one or more antisense compound. In certain embodiments, such pharmaceutical composition comprises a sterile saline solution and one or more antisense compound. In certain embodiments, such pharmaceutical composition consists of a sterile saline solution and one or more antisense compound.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments antisense compounds, can be utilized in pharmaceutical compositions by combining such oligomeric compounds with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in certain embodiments, employed in the methods described herein is a pharmaceutical composition comprising an antisense compound and a pharmaceutically acceptable diluent. In certain embodiments, the pharmaceutically acceptable diluent is PBS.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid-based vectors have been used in nucleic acid therapies in a variety of methods. For example, in one method, the nucleic acid is introduced into preformed liposomes or lipoplexes made of mixtures of cationic lipids and neutral lipids. In another method, DNA complexes with mono- or poly-cationic lipids are formed without the presence of a neutral lipid.

Certain preparations are described in Akinc et al., *Nature Biotechnology* 26, 561-569 (1 May 2008), which is herein incorporated by reference in its entirety.

5. Administration to a Subject

In certain embodiments, pharmaceutical compositions comprising one or more antisense compound are administered to a subject. In certain embodiments, such pharmaceutical compositions are administered by injection. In certain embodiments, such pharmaceutical compositions are administered by infusion.

In certain embodiments, pharmaceutical compositions are administered by injection or infusion into the CSF. In certain such embodiments, pharmaceutical compositions are administered by direct injection or infusion into the spine. In certain embodiments, pharmaceutical compositions are administered by injection or infusion into the brain. In certain embodiments, pharmaceutical compositions are administered by intrathecal injection or infusion rather than into the spinal cord tissue itself. Without being limited as to theory, in certain embodiments, the antisense compound released into the surrounding CSF and may penetrate into the spinal cord parenchyma. An additional advantage of intrathecal delivery is that the intrathecal route mimics lumbar puncture administration (i.e., spinal tap) already in routine use in humans.

In certain embodiments, pharmaceutical compositions are administered by intracerebroventricular (ICV) injection or infusion. Intracerebroventricular, or intraventricular, delivery of a pharmaceutical composition comprising one or more antisense compounds may be performed in any one or more of the brain's ventricles, which are filled with cerebrospinal fluid (CSF). CSF is a clear fluid that fills the ventricles, is present in the subarachnoid space, and surrounds the brain and spinal cord. CSF is produced by the choroid plexuses and via the weeping or transmission of tissue fluid by the brain into the ventricles. The choroid plexus is a structure lining the floor of the lateral ventricle and the roof of the third and fourth ventricles. Certain studies have indicated that these structures are capable of producing 400-600 ccs of fluid per day consistent with an amount to fill the central nervous system spaces four times in a day. In adult humans, the volume of this fluid has been calculated to be from 125 to 150 ml (4-5 oz). The CSF is in continuous formation, circulation and absorption. Certain studies have indicated that approximately 430 to 450 ml (nearly 2 cups) of CSF may be produced every day. Certain calculations estimate that production equals approximately 0.35 ml per minute in adults and 0.15 per minute in infant humans. The choroid plexuses of the lateral ventricles produce the majority of CSF. It flows through the foramina of Monro into the third ventricle where it is added to by production from the third ventricle and continues down through the aqueduct of Sylvius to the fourth ventricle. The fourth ventricle adds more CSF; the fluid then travels into the subarachnoid space through the foramina of Magendie and Luschka. It then circulates throughout the base of the brain, down around the spinal cord and upward over the cerebral hemispheres. The CSF empties into the blood via the arachnoid villi and intracranial vascular sinuses.

In certain embodiments, such pharmaceutical compositions are administered systemically. In certain embodiments, pharmaceutical compositions are administered subcutaneously. In certain embodiments, pharmaceutical compositions are administered intravenously. In certain embodiments, pharmaceutical compositions are administered by intramuscular injection.

In certain embodiments, pharmaceutical compositions are administered both directly to the CSF (e.g., IT and/or ICV injection and/or infusion) and systemically.

In certain embodiments, an antisense compound administered systemically enters neurons. In certain embodiments, systemically administered antisense compounds may penetrate the blood-brain barrier, particularly in young subjects where the blood-brain barrier is not fully formed (e.g., in subjects in eutero and/or in newborn subjects). In certain embodiments, some amount of systemically administered antisense compound may be taken up by nerve cells, even in subjects in which the blood-brain barrier is fully formed. For example, antisense compounds may enter a neuron at or near the neuromuscular junction (retrograde uptake). In certain embodiments, such retrograde uptake results in antisense activity inside the neuron, including, but not limited to, a motor neuron, and provides a therapeutic benefit by antisense activity inside the neuron.

In certain embodiments, systemic administration provides therapeutic benefit by antisense activity occurring in cells and/or tissues other than neurons. While evidence suggests that functional SMN inside neurons is required for normal neuron function, the consequence of reduced functional SMN in other cells and tissues is not well characterized. In certain embodiments, antisense activity in non-neuronal cells results in restoration of SMN function in those non-neuronal cells, which in turn results in therapeutic benefit.

In certain embodiments, improved SMN function in non-neuronal cells provides improved neuronal cell function, whether or not SMN function inside neurons is improved. For example, in certain embodiments, systemic administration of pharmaceutical compositions of the present invention results in antisense activity in muscle cells. Such antisense activity in muscle cells may provide a benefit to the motor-neurons associated with that muscle cell or to neurons generally. In such embodiments, the muscle cell having restored SMN function may provide a factor that improves neuronal viability and/or function. In certain embodiments, such antisense activity is independent of benefit from antisense activity occurring from antisense compounds inside neurons. In certain embodiments, systemic administration of pharmaceutical compositions of the present invention results in antisense activity in other non-neuronal cells, including cells not in immediate association with neurons. Such antisense activity in non-neuronal cells may improve function of neurons. For example, antisense activity in a non-neuronal cell (e.g., liver cell) may result in that cell producing a factor that improves function of neurons. Note: since the term "antisense activity" includes direct and indirect activities, a benefit to neuronal function is an "antisense activity" even if no antisense compound enters the neuron.

In certain embodiments, systemic administration of a pharmaceutical composition results in therapeutic benefit independent of direct or indirect antisense activities in neurons. Typically, in the setting of SMA, neuronal function is diminished, resulting in significant symptoms. Additional symptoms may result from diminished SMN activity in other cells. Certain such symptoms may be masked by the relative severity of symptoms from diminished neuronal function. In certain embodiments, systemic administration results in restored or improved SMN function in non-neuronal cells. In certain such embodiments, such restored or improved SMN function in non-neuronal cells has therapeutic benefit. For example, in certain instances, subjects having SMA have reduced growth. Such reduced growth may not result from diminished function in neuronal cells. Indeed, reduced growth may be related to impaired function of cells in another organ, such as the pituitary gland, and/or may be the result of SMN deficiencies throughout the cells of the body. In such embodiments, systemic administration may result in improved SMN activity in pituitary cells and/or other cells, resulting in improved growth. In certain instances, administration to the CSF restores sufficient neuronal function to allow a subject to live longer, however one or more symptoms previously unknown because subjects typically died before such symptoms appeared emerges, because the subject lives longer. Certain such emergent symptoms may be lethal. In certain embodiments, emergent symptoms are treated by systemic administration. Regardless of mechanism, in certain embodiments, a variety of symptoms of SMA, including, but not limited to symptoms previously masked by more severe symptoms associated with impaired neuronal function, may be treated by systemic administration.

In certain embodiments, systemic administration of pharmaceutical compositions of the present invention result in increased SMN activity in muscle cells. In certain embodiments, such improved SMN activity in muscle cells provides therapeutic benefit. Improved SMN activity in muscle alone has been reported to be insufficient to provide therapeutic benefit (e.g., Gravrilina, et al., Hum Mol Genet 2008 17(8): 1063-1075). In certain embodiments, the present invention provides methods that result improve SMN function in muscle and do provide therapeutic benefit. In certain instances, therapeutic benefit may be attributable to improved SMN function in other cells (alone or in combination with muscle cells). In certain embodiments, improved SMN function in muscle alone may provide benefit.

In certain embodiments, systemic administration results in improved survival.

6. Spinal Muscular Atrophy (SMA)

SMA is a genetic disorder characterized by degeneration of spinal motor neurons. SMA is caused by the homozygous loss of both functional copies of the SMN1 gene. However, the SMN2 gene has the potential to code for the same protein as SMN1 and thus overcome the genetic defect of SMA patients. SMN2 contains a translationally silent mutation (C→T) at position +6 of exon 7, which results in inefficient inclusion of exon 7 in SMN2 transcripts. Therefore, the predominant form of SMN2, one which lacks exon 7, is unstable and inactive. Thus, therapeutic compounds capable of modulating SMN2 splicing such that the percentage of SMN2 transcripts containing exon 7 is increased, would be useful for the treatment of SMA.

In certain embodiments, the present invention provides antisense compounds complementary to a pre-mRNA encoding SMN2. In certain such embodiments, the antisense compound alters splicing of SMN2. Certain sequences and regions useful for altering splicing of SMN2 may be found in PCT/US06/024469, which is hereby incorporated by reference in its entirety for any purpose. In certain embodiments, oligomeric compounds having any motif described herein have a nucleobase sequence complementary to intron 7 of SMN2. Certain such nucleobase sequences are exemplified in the non-limiting table below.

| Sequence | Length | SEQ ID |
|---|---|---|
| TGCTGGCAGACTTAC | 15 | 3 |
| CATAATGCTGGCAGA | 15 | 4 |
| TCATAATGCTGGCAG | 15 | 5 |
| TTCATAATGCTGGCA | 15 | 6 |
| TTTCATAATGCTGGC | 15 | 2 |
| ATTCACTTTCATAATGCTGG | 20 | 7 |
| TCACTTTCATAATGCTGG | 18 | 1 |
| CTTTCATAATGCTGG | 15 | 8 |
| TCATAATGCTGG | 12 | 9 |
| ACTTTCATAATGCTG | 15 | 10 |
| TTCATAATGCTG | 12 | 11 |
| CACTTTCATAATGCT | 15 | 12 |
| TTTCATAATGCT | 12 | 13 |
| TCACTTTCATAATGC | 15 | 14 |
| CTTTCATAATGC | 12 | 15 |
| TTCACTTTCATAATG | 15 | 16 |
| ACTTTCATAATG | 12 | 17 |
| ATTCACTTTCATAAT | 15 | 18 |
| CACTTTCATAAT | 12 | 19 |
| GATTCACTTTCATAA | 15 | 20 |
| TCACTTTCATAA | 12 | 21 |
| TTCACTTTCATA | 12 | 22 |
| ATTCACTTTCAT | 12 | 23 |
| AGTAAGATTCACTTT | 15 | 24 |

Antisense compounds of the present invention can be used to modulate the expression of SMN2 in a subject, such as a human. In certain embodiments, the subject has spinal muscular atrophy. In certain such subjects, the SMN1 gene is absent or otherwise fails to produce sufficient amounts of functional SMN protein. In certain embodiments, the antisense compounds of the present invention effectively modulate splicing of SMN2, resulting in an increase in exon 7 inclusion in SMN2 mRNA and ultimately in SMN2 protein that includes the amino acids corresponding to exon 7. Such alternate SMN2 protein resembles wild-type SMN protein. Antisense compounds of the present invention that effectively modulate expression of SMN2 mRNA or protein products of expression are considered active antisense compounds.

Modulation of expression of SMN2 can be measured in a bodily fluid, which may or may not contain cells; tissue; or organ of the animal. Methods of obtaining samples for analysis, such as body fluids (e.g., sputum, serum, CSF), tissues (e.g., biopsy), or organs, and methods of preparation of the samples to allow for analysis are well known to those skilled in the art. Methods for analysis of RNA and protein levels are discussed above and are well known to those skilled in the art. The effects of treatment can be assessed by measuring biomarkers associated with the target gene expression in the aforementioned fluids, tissues or organs, collected from an animal contacted with one or more compounds of the invention, by routine clinical methods known in the art.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of SMN2 expression in the cells of bodily fluids, organs or tissues. An effective amount can be determined by monitoring the modulatory effect of the antisense compound or compounds or compositions on target nucleic acids or their products by methods routine to the skilled artisan.

The invention also provides an antisense compound as described herein, for use in any of the methods as described herein. For example, the invention provides an antisense compound comprising an antisense oligonucleotide complementary to a nucleic acid encoding human SMN2, for use in treating a disease or condition associated with survival motor neuron protein (SMN), such as spinal muscular atrophy (SMA). As a further example, the invention provides an antisense compound comprising an antisense oligonucleotide complementary to a nucleic acid encoding human SMN2, for use in treating a disease or condition associated with survival motor neuron protein (SMN) by administering the antisense compound directly into the central nervous system (CNS) or CSF.

The invention also provides the use of an antisense compound as described herein in the manufacture of a medicament for use in any of the methods as described herein. For example, the invention provides the use of an antisense compound comprising an antisense oligonucleotide complementary to a nucleic acid encoding human SMN2 in the manufacture of a medicament for treating a disease or condition associated with survival motor neuron protein (SMN), such as spinal muscular atrophy (SMA). As a further example, the invention provides the use of an antisense compound comprising an antisense oligonucleotide complementary to a nucleic acid encoding human SMN2 in the manufacture of a medicament for treating a disease or condition associated with survival motor neuron protein (SMN) by administration of the medicament directly into the central nervous system (CNS) or CSF.

In certain embodiments, oligomeric compounds having any motif described herein have a nucleobase sequence complementary to exon 7 of SMN2.

In certain embodiments, oligomeric compounds having any motif described herein have a nucleobase sequence complementary to intron 6 of SMN2.

In certain embodiments, an antisense compound comprises an antisense oligonucleotide having a nucleobase sequence comprising at least 10 nucleobases of the sequence: TCACTTTCATAATGCTGG (SEQ ID NO: 1). In certain embodiments, an antisense oligonucleotide has a nucleobase sequence comprising at least 11 nucleobases of such sequence. In certain embodiments, an antisense oligonucleotide has a nucleobase sequence comprising at least 12 nucleobases of such sequence. In certain embodiments, an antisense oligonucleotide has a nucleobase sequence comprising at least 13 nucleobases of such sequence. In certain embodiments, an antisense oligonucleotide has a nucleobase sequence comprising at least 14 nucleobases of such sequence. In certain embodiments, an antisense oligonucleotide has a nucleobase sequence comprising at least 15 nucleobases of such sequence. In certain embodiments, an antisense oligonucleotide has a nucleobase sequence comprising at least 16 nucleobases of such sequence. In certain embodiments, an antisense oligonucleotide has a nucleobase sequence comprising at least 17 nucleobases of such sequence. In certain embodiments, an antisense oligonucleotide has a nucleobase sequence comprising the nucleobases of such sequence. In certain embodiments, an antisense oligonucleotide has a nucleobase sequence consisting of the nucleobases of such sequence. In certain embodiments, an antisense oligonucleotide consists of 10-18 linked nucleosides and has a nucleobase sequence 100% identical to an equal-length portion of the sequence:

```
                              (SEQ ID NO: 1)
TCACTTTCATAATGCTGG.
```

7. Certain Subjects

In certain embodiments, a subject has one or more indicator of SMA. In certain embodiments, the subject has reduced electrical activity of one or more muscles. In certain embodiments, the subject has a mutant SMN1 gene. In certain embodiment, the subject's SMN1 gene is absent or incapable of producing functional SMN protein. In certain embodiments, the subject is diagnosed by a genetic test. In certain embodiments, the subject is identified by muscle biopsy. In certain embodiments, a subject is unable to sit upright. In certain embodiments, a subject is unable to stand or walk. In certain embodiments, a subject requires assistance to breathe and/or eat. In certain embodiment, a subject is identified by electrophysiological measurement of muscle and/or muscle biopsy.

In certain embodiments, the subject has SMA type I. In certain embodiments, the subject has SMA type II. In certain embodiments, the subject has SMA type III. In certain embodiments, the subject is diagnosed as having SMA in utero. In certain embodiments, the subject is diagnosed as having SMA within one week after birth. In certain embodiments, the subject is diagnosed as having SMA within one month of birth. In certain embodiments, the subject is diagnosed as having SMA by 3 months of age. In certain embodiments, the subject is diagnosed as having SMA by 6 months of age. In certain embodiments, the subject is diagnosed as having SMA by 1 year of age. In certain embodiments, the subject is diagnosed as having SMA between 1 and 2 years of age. In certain embodiments, the subject is diagnosed as having SMA between 1 and 15 years of age. In certain embodiments, the subject is diagnosed as having SMA when the subject is older than 15 years of age.

In certain embodiments, the first dose of a pharmaceutical composition according to the present invention is administered in utero. In certain such embodiments, the first dose is administered before complete development of the blood-brain-barrier. In certain embodiments, the first dose is administered to the subject in utero systemically. In certain embodiments, the first dose is administered in utero after formation of the blood-brain-barrier. In certain embodiments, the first dose is administered to the CSF.

In certain embodiments, the first dose of a pharmaceutical composition according to the present invention is administered when the subject is less than one week old. In certain embodiments, the first dose of a pharmaceutical composition according to the present invention is administered when the subject is less than one month old. In certain embodiments, the first dose of a pharmaceutical composition according to the present invention is administered when the subject is less than 3 months old. In certain embodiments, the first dose of a pharmaceutical composition according to the present invention is administered when the subject is less than 6 months old. In certain embodiments, the first dose of a pharmaceutical composition according to the present invention is administered when the subject is less than one year old. In certain embodiments, the first dose of a pharmaceutical composition according to the present invention is administered when the subject is less than 2 years old. In certain embodiments, the first dose of a pharmaceutical composition according to the present invention is administered when the subject is less than 15 years old. In certain embodiments, the first dose of a pharmaceutical composition according to the present invention is administered when the subject is older than 15 years old.

8. Certain Doses

In certain embodiments, the present invention provides dose amounts and frequencies. In certain embodiments, pharmaceutical compositions are administered as a bolus injection. In certain such embodiments, the dose of the bolus injection is from 0.01 to 25 milligrams of antisense compound per kilogram body weight of the subject. In certain such embodiments, the dose of the bolus injection is from 0.01 to 10 milligrams of antisense compound per kilogram body weight of the subject. In certain embodiments, the dose is from 0.05 to 5 milligrams of antisense compound per kilogram body weight of the subject. In certain embodiments, the dose is from 0.1 to 2 milligrams of antisense compound per kilogram body weight of the subject. In certain embodiments, the dose is from 0.5 to 1 milligrams of antisense compound per kilogram body weight of the subject. In certain embodiments, such doses are administered twice monthly. In certain embodiments, such doses are administered every month. In certain embodiments, such doses are administered every 2 months. In certain embodiments, such doses are administered every 6 months. In certain embodiments, such doses are administered by bolus injection into the CSF. In certain embodiments, such doses are administered by intrathecal bolus injection. In certain embodiments, such doses are administered by bolus systemic injection (e.g., subcutaneous, intramuscular, or intravenous injection). In certain embodiments, subjects receive bolus injections into the CSF and bolus systemic injections. In such embodiments, the doses of the CSF bolus and the systemic bolus may be the same or different from one another. In certain embodiments, the CSF and systemic doses are administered at different frequencies. In certain embodiments, the invention provides a dosing regimen comprising at least one bolus intrathecal injection and at least one bolus subcutaneous injection.

In certain embodiments, pharmaceutical compositions are administered by continuous infusion. Such continuous infusion may be accomplished by an infusion pump that delivers pharmaceutical compositions to the CSF. In certain embodiments, such infusion pump delivers pharmaceutical composition IT or ICV. In certain such embodiments, the dose administered is between 0.05 and 25 milligrams of antisense compound per kilogram body weight of the subject per day. In certain embodiments, the dose administered is from 0.1 to 10 milligrams of antisense compound per kilogram body weight of the subject per day. In certain embodiments, the dose administered is from 0.5 to 10 milligrams of antisense compound per kilogram body weight of the subject per day. In certain embodiments, the dose administered is from 0.5 to 5 milligrams of antisense compound per kilogram body weight of the subject per day. In certain embodiments, the dose administered is from 1 to 5 milligrams of antisense compound per kilogram body weight of the subject per day. In certain embodiments, the invention provides a dosing regimen comprising infusion into the CNS and at least one bolus systemic injection. In certain embodiments, the invention provides a dosing regimen comprising infusion into the CNS and at least one bolus subcutaneous injection. In certain embodiments, the dose, whether by bolus or infusion, is adjusted to achieve or maintain a concentration of antisense compound from 0.1 to 100 microgram per gram of CNS tissue. In certain embodiments, the dose, whether by bolus or infusion, is adjusted to achieve or maintain a concentration of antisense compound from 1 to 10 microgram per gram of CNS tissue. In certain embodiments, the dose, whether by bolus or infusion, is adjusted to achieve or maintain a concentration of antisense compound from 0.1 to 1 microgram per gram of CNS tissue.

In certain embodiments, dosing a subject is divided into an induction phase and a maintenance phase. In certain such embodiments, the dose administered during the induction phase is greater than the dose administered during the maintenance phase. In certain embodiments, the dose administered during the induction phase is less than the dose administered during the maintenance phase. In certain embodiments, the induction phase is achieved by bolus injection and the maintenance phase is achieved by continuous infusion.

In certain embodiments, the invention provides systemic administration of antisense compounds, either alone or in combination with delivery into the CSF. In certain embodiments, the dose for systemic administration is from 0.1 mg/kg to 200 mg/kg. In certain embodiments, the dose for systemic administration is from 0.1 mg/kg to 100 mg/kg. In certain embodiments, the dose for systemic administration is from 0.5 mg/kg to 100 mg/kg. In certain embodiments, the dose for systemic administration is from 1 mg/kg to 100 mg/kg. In certain embodiments, the dose for systemic administration is from 1 mg/kg to 50 mg/kg. In certain embodiments, the dose for systemic administration is from 1 mg/kg to 25 mg/kg. In certain embodiments, the dose for systemic administration is from 0.1 mg/kg to 25 mg/kg. In certain embodiments, the dose for systemic administration is from 0.1 mg/kg to 10 mg/kg. In certain embodiments, the dose for systemic administration is from 1 mg/kg to 10 mg/kg. In certain embodiments, the dose for systemic administration is from 1 mg/kg to 5 mg/kg. In certain embodiments comprising both systemic and CSF delivery, the doses for those two routes are independently determined.

a. Calculation of Appropriate Human Doses

In certain embodiments, the subject is a human. In certain embodiments, a human dose is calculated or estimated from data from animal experiments, such as those described herein. In certain embodiments, a human dose is calculated or estimated from data from monkey and/or mouse experiments, such as those described herein. In certain embodiments, a human dose is calculated or estimated from data from mouse experiments, such as those described herein. In certain embodiments, appropriate human doses can be calculated using pharmacokinetic data from mouse along with knowledge of brain weight and/or cerebrospinal fluid (CSF) turnover rates. For example, the mouse brain weight is approximately 0.4 g, which is approximately 2% of its body weight. In humans, the average brain weight is 1.5 kg which is approximately 2.5% of body weight. In certain embodiments, administration into the CSF results in elimination of a portion of the compound through uptake in brain tissue and subsequent metabolism. By using the ratio of human to mouse brain weight as a scaling factor an estimate of the elimination and clearance through the brain tissue can be calculated. Additionally, the CSF turnover rate can be used to estimate elimination of compound from the CSF to blood. Mouse CSF turnover rate is approximately 10-12 times per day (0.04 mL produced at 0.325 µl/min). Human CSF turnover rate is approximately 4 times per day (100-160 mL produced at 350-400 µl/min). Clearance, and therefore dosing requirements, can be based on brain weight elimination scaling, and/or the CSF turnover scaling. The extrapolated human CSF clearance can be used to estimate equivalent doses in humans that approximate doses in mice. In this way, human doses can be estimated that account for differences in tissue metabolism based on brain weight and CSF turnover rates. Such methods of calculation and estimate are known to those skilled in the art.

By way of non-limiting example, in certain embodiments, an equivalent human dose can be estimated from a desired mouse dose by multiplying the mg/kg mouse dose by a factor from about 0.25 to about 1.25 depending on the determined clearance and elimination of a particular compound. Thus, for example, in certain embodiments, a human dose equivalent of a 0.01 mg dose for a 20 g mouse will range from about 8.75 mg to about 43.75 mg total dose for a 70 kg human. Likewise, in certain embodiments, a human dose equivalent of a 0.01 mg dose for a 4 g newborn mouse will range from about 1.9 mg to about 9.4 mg total dose for a 3 kg newborn human. These example doses are merely to illustrate how one of skill may determine an appropriate human dose and are not intended to limit the present invention.

In certain embodiments, a human dose for systemic delivery (whether administered alone or in combination with CSF delivery) is calculated or estimated from data from animal experiments, such as those described herein. Typically, an appropriate human dose (in mg/kg) for systemic dose is between 0.1 and 10 times an effective dose in animals. Thus, solely for example, a subcutaneous dose of 50 µg in a 2 g newborn mouse is a dose of 25 mg/kg. The corresponding dose for a human is predicted to be between 2.5 mg/kg and 250 mg/kg. For a 3 kilogram infant, the corresponding dose is between 7.5 mg and 750 mg. For a 25 kg child, the corresponding dose is from 62.5 mg to 6250 mg.

9. Treatment Regimens

In certain embodiments, the above dose amounts, dose frequencies, routes of administration, induction and maintenance phases, and timing of first dose are combined to provide dosing regimens for subjects having SMA. Such dosing regimens may be selected and adjusted to provide amelioration of one or more symptom of SMA and/or to reduce or avoid toxicity or side effects attributable to the administration of the pharmaceutical composition. In certain embodiments, subjects are in utero or newborn. In such embodiments, administration of pharmaceutical compositions, particularly by continuous infusion, presents particular challenges. Accordingly, in certain embodiments, the present invention provides for administration of pharmaceutical compositions by bolus administration while the subject is in utero or very young, followed by continuous infusion via an implanted infusion pump when the subject is older and placement of such pump is more practical. Further, in certain embodiments, as a subject grows, the absolute dose is increased to achieve the same or similar dose:body-weight ratio. The following table is intended to exemplify treatment regimens and is not intended to limit the possible combinations of treatments which will be easily accomplished by one of skill in the art.

| Dosing period | First | Second | Third | Fourth | Fifth |
|---|---|---|---|---|---|
| Regimen 1 | | | | | |
| Subject Age | In utero, prior to formation of blood-brain-barrier | In utero, after formation of blood-brain-barrier | >1 week | 6 months | 1.5 years |
| Dose Amount | 50 µg | 50 µg | 100 µg | 10 µg/day | 50 µg/day |
| Frequency | Single admin | Single admin | Monthly | Continuous | Continuous |
| Route of Administration | Systemic injection | IT injection | IT injections | IT infusion | IT infusion |
| Duration | N/A | N/A | 6 months | 1 year | Ongoing |
| Regimen 2 | | | | | |
| Subject Age | In utero, after formation of blood-brain-barrier | >1 week | 6 months | 1.5 years | N/A |
| Dose Amount | 50 µg | 100 µg | 5 mg/day | 10 mg/day | N/A |
| Frequency | Single admin | Monthly | Continuous | Continuous | N/A |
| Route of Administration | ICV injection | ICV injection | ICV infusion | ICV infusion | N/A |
| Duration | N/A | 6 months | 1 year | Ongoing | N/A |
| Regimen 3 | | | | | |
| Subject Age | >1 week | 6 months | 1.5 years | | 2.5 years* |
| Dose Amount | 100 µg | 500 µg/day | 20 mg/day | 20 mg/day | 100 mg |
| Frequency | 2xMonthly | Continuous | Continuous | Continuous | 2xMonthly |
| Route of Administration | ICV injection | ICV infusion | ICV infusion | ICV infusion | IP |
| Duration | 6 months | 1 year | 1 year | Ongoing | Ongoing |

*Note:
the 4$^{th}$ dosing period in regimen 3 exemplifies continuous CSF infusion combined with periodic systemic administration. These treatment regimens are intended to exemplify and not to limit the present invention.

In certain embodiments, the dosing regimen comprises a systemic administration, either alone or in combination with administration into the CSF (for example regimen 3, above). The table, below further exemplifies such regimens.

| Systemic administration | | | CSF administration | | |
|---|---|---|---|---|---|
| Dose | Route | Frequency | Dose | Route | Frequency |
| 1-5 mg/kg | subcutaneous | weekly | 5-10 mg/kg | bolus IT | monthly |
| 1-5 mg/kg | subcutaneous | monthly | 1-5 mg/kg | bolus ICV | 2 months |
| 10-50 mg/kg | subcutaneous | monthly | 0.5-1 mg/kg | bolus IT | 6 months |
| 0.5-25 mg/kg | subcutaneous | monthly | 10 mg/kg/day | IT infusion | continuous for 7 days every 6 months |
| 0.1-10 mg/kg | subcutaneous | monthly | | none | |
| none | | | 0.5-1 mg/kg | bolus IT | 6 months |

These treatment regimens are intended to exemplify and not to limit the present invention. One of skill in the art will be able to select an appropriate combination of the doses and deliveries in view of the present disclosure and based on a variety of factors, such as the severity of the condition and the overall health and age of the subject.

10. Co-Administration

In certain embodiments, pharmaceutical compositions of the present invention are co-administered with at least one other pharmaceutical composition for treating SMA and/or for treating one or more symptom associated with SMA. In certain embodiments, such other pharmaceutical composition is selected from trichostatin-A, valproic acid, riluzole, hydroxyurea, and a butyrate or butyrate derivative. In certain embodiments, pharmaceutical compositions of the present invention are co-administered with trichostatin A. In certain embodiments, pharmaceutical compositions of the present invention are co-administered with a derivative of quinazoline, for example as described in Thurmond, et al., J. Med Chem. 2008, 51, 449-469. In certain embodiments, a pharmaceutical composition of the present invention and at least one other pharmaceutical composition are co-administered at the same time. In certain embodiments, a pharmaceutical composition of the present invention and at least one other pharmaceutical composition are co-administered at different times.

In certain embodiments, pharmaceutical compositions of the present invention are co-administered with a gene therapy agent. In certain such embodiments, the gene therapy agent is administered to the CSF and the pharmaceutical composition of the present invention is administered systemically. In certain such embodiments, the gene therapy agent is administered to the CSF and the pharmaceutical composition of the present invention is administered to the CSF and systemically. In certain embodiments, a pharmaceutical composition of the present invention and a gene therapy agent are co-administered at the same time. In certain embodiments, a pharmaceutical composition of the present invention and a gene therapy agent are co-administered at different times. Certain gene therapy approaches to SMA treatment have been reported (e.g., Coady et al., PLoS ONE 2008 3(10): e3468; Passini et al., J Clin Invest 2010 Apr. 1, 120(4): 1253-64).

In certain embodiments, pharmaceutical compositions of the present invention are co-administered with at least one other therapy for SMA. In certain embodiments, such other therapy for SMA is surgery. In certain embodiments, such other therapy is physical therapy, including, but not limited to exercises designed to strengthen muscles necessary for breathing, such as cough therapy. In certain embodiments, other therapy is a physical intervention, such as a feeding tube or device for assisted breathing.

In certain embodiments, pharmaceutical compositions of the present invention are co-administered with one or more other pharmaceutical compositions that reduce an undesired side-effect of the pharmaceutical compositions of the present invention.

11. Phenotypic Effects

In certain embodiments, administration of at least one pharmaceutical composition of the present invention results in a phenotypic change in the subject. In certain embodiments, such phenotypic changes include, but are not limited to: increased absolute amount of SMN mRNA that includes exon 7; increase in the ratio SMN mRNA that includes exon 7 to SMN mRNA lacking exon 7; increased absolute amount of SMN protein that includes exon 7; increase in the ratio SMN protein that includes exon 7 to SMN protein lacking exon 7; improved muscle strength, improved electrical activity in at least one muscle; improved respiration; weight gain; and survival. In certain embodiments, at least one phenotypic change is detected in a motoneuron of the subject. In certain embodiments, administration of at least one pharmaceutical composition of the present invention results in a subject being able to sit-up, to stand, and/or to walk. In certain embodiments, administration of at least one pharmaceutical composition of the present invention results in a subject being able to eat, drink, and/or breathe without assistance. In certain embodiments, efficacy of treatment is assessed by electrophysiological assessment of muscle. In certain embodiments, administration of a pharmaceutical composition of the present invention improves at least one symptom of SMA and has little or no inflammatory effect. In certain such embodiment, absence of inflammatory effect is determined by the absence of significant increase in Aif1 levels upon treatment.

In certain embodiments, administration of at least one pharmaceutical composition of the present invention delays the onset of at least one symptom of SMA. In certain embodiments, administration of at least one pharmaceutical composition of the present invention slows the progression of at least one symptom of SMA. In certain embodiments, administration of at least one pharmaceutical composition of the present invention reduces the severity of at least one symptom of SMA.

In certain embodiments, administration of at least one pharmaceutical composition of the present invention results in an undesired side-effect. In certain embodiments, a treatment regimen is identified that results in desired amelioration of symptoms while avoiding undesired side-effects.

12. Dosage Units

In certain embodiments pharmaceutical compositions of the present invention are prepared as dosage units for administration. Certain such dosage units are at concentrations selected from 0.01 mg to 100 mg. In certain such embodiments, a pharmaceutical composition of the present invention comprises a dose of antisense compound selected from 0.01 mg, 0.1 mg, 0.5 mg, 1 mg, 5 mg, 10 mg, 20 mg, 25 mg, 50 mg, 75 mg, 100 mg, 150 mg, and 200 mg. In certain embodiments, a pharmaceutical composition is comprises a dose of oligonucleotide selected from 0.1 mg, 0.5 mg, 1 mg, 5 mg, 10 mg, 25 mg, and 50 mg.

13. Kits

In certain embodiments, the present invention provides kits comprising at least one pharmaceutical composition. In certain embodiments, such kits further comprise a means of delivery, for example a syringe or infusion pump.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited herein is hereby incorporated by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified bases, such as "AT$^{me}$C-GAUCG," wherein $^{me}$C indicates a cytosine base comprising a methyl group at the 5-position.

EXAMPLE 1

Antisense Compounds Targeting SMN2

The following oligonucleotides were synthesized using standard techniques previously reported.

| Reference # | Sequence | Length | Chemistry | SEQ ID |
|---|---|---|---|---|
| ISIS396443 | TCACTTTCATAATGCTGG | 18 | Full 2'-MOE; full PS | 1 |
| ISIS396449 | TTTCATAATGCTGGC | 15 | Full 2'-MOE; full PS | 2 |

PS = phosphorothioate internucleoside linkages

EXAMPLE 2

Smn−/− SMN Transgenic Mice

Therapeutic effectiveness and safety using the antisense compounds as described above can be tested in an appropriate animal model. For example, animal models which appear most similar to human disease include animal species which either spontaneously develop a high incidence of the particular disease or those that have been induced to do so.

In particular, animal models for SMA are known. As explained above, the molecular basis of SMA, an autosomal recessive neuromuscular disorder, is the homozygous loss of the survival motor neuron gene 1 (SMN1). A nearly identical copy of the SMN1 gene, called SMN2 is found in humans and modulates the disease severity. In contrast to humans, mice have a single gene (Smn) that is equivalent to SMN1. Homozygous loss of this gene is lethal to embryos and results in massive cell death, which indicates that the Smn gene product is necessary for cellular survival and function. The introduction of 2 copies of SMN2 into mice lacking SMN rescues the embryonic lethality, resulting in mice with the SMA phenotype (Monani et al., *Hum. Mol. Genet.* (2000) 9:333-339. A high copy number of SMN2 rescues the mice because sufficient SMN protein is produced in motor neurons. See, also, Hsieh-Li, et al., Nat. Genet. (2000) 24:66-70, reporting the production of transgenic mouse lines that expressed human SMN2. In particular, transgenic mice harboring SMN2 in the Smn−/− background showed pathological changes in the spinal cord and skeletal muscles similar to those of SMA patients. The severity of the pathological changes in these mice correlated with the amount of SMN protein that contained the region encoded by exon 7. Heterozygous mice lacking one copy of Smn are designated Smn−/+ and are a model for the less severe form of SMA, type III.

The severity of the SMA phenotype is a function of the number of copies of human SMN2 in the mice. The "Taiwan" strain has 4 copies of human SMN2, resulting in mice that have moderate to severe SMA phenotype, similar to Type I or Type II.

Delta-7 mice (Smn$^{−/−}$, hSMN2$^{+/+}$, SMNΔ7$^{+/+}$) also lack mouse Smn and express human SMN2. Delta 7 mice have a more severe phenotype and die shortly after birth, typically about 15-20 days after birth.

EXAMPLE 3

Systemic Administration of Antisense Compounds In Vivo in Smn−/− SMN2 (Taiwan Strain)

Taiwan mice were treated by intraperitoneal injection with saline or with 35 mg/kg of ISIS396443 or a mismatched antisense oligonucleotide control once each day for 5 days and were sacrificed 2 days later on day 7. Liver and kidney were collected and RNA was isolated using standard techniques. SMN2 with and without exon 7 was visualized by RT-PCR. Administration with ISIS396443 resulted in substantial increase in exon 7 inclusion in the SMN2 from kidney and liver compared to saline and mismatch control treated animals.

EXAMPLE 4

Intracerebroventricular (ICV) Administration of Antisense Compounds In Vivo in Smn−/− SMN2 (Taiwan Strain)

Taiwan mice were injected ICV either with saline or with 150 μg of ISIS396443 each day for 7 days. The mice were sacrificed on day 8 and RNA from brain and spinal cord was extracted. RT-PCR analysis showed substantial increase in exon 7 inclusion in the SMN2 in brain and spinal cord samples obtained from animals treated with ISIS396443. These results indicate that ICV treatment with antisense oligonucleotide targeting SMN can rescue the SMA condition because exclusion of exon 7 is associated with the SMA phenotype.

Dose-Response

Taiwan mice were injected ICV either with saline or with 10, 50, 100, or 150 μg of ISIS396443 each day for 7 days (5 mice in each treatment group) and were sacrificed on day 8. RNA was isolated and analyzed by RT-PCR. The 10 μg treatment group showed moderate exon 7 inclusion. The 50 μg, 100 μg, and 150 μg groups all showed substantial exon 7 inclusion.

Duration of Response

To determine the duration of effect, 24 mice were injected ICV with 50 μg of ISIS396443 each day for 7 days. Four mice were sacrificed at the time of the final dose (time 0) and four mice were sacrificed at each of: 1 week, 2 weeks, 4 weeks and 8 weeks after the final dose. All treated mice showed substantial exon 7 inclusion by RT-PCR with the effect at week 8 showing no difference with the other groups, as shown in FIG. 1:

These results indicate that ICV administration of ISIS396443 at 50 μg per day for 7 days is effective for at least 8 weeks following treatment.

Figure 2:
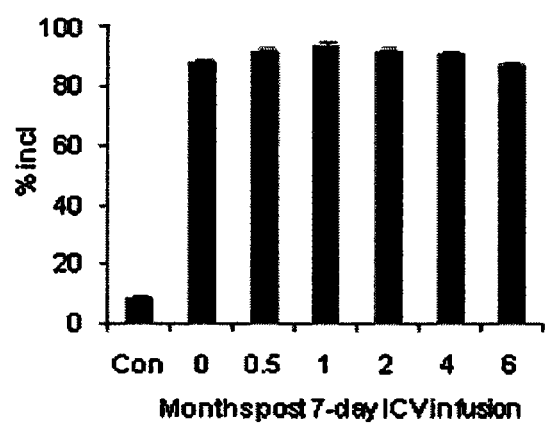
FIG. 2 shows results from a duration of action study discussed in Example 4, in which the percent of SMN2 that includes exon 7 was assessed at 0, 0.5, 1, 2, 5, and 6 months after termination of 7 days of treatment. The month "0" sample was taken 1 day after termination of treatment. CON represents saline treated mice. There was no difference in % inclusion among control saline treated mice at different time points from 0 to 6 months.

The experiment was repeated to test longer time points. Type III mice were treated by ICV infusion of ISIS396443 at 50 µg/day for 7 days. Mice were sacrificed 0, 0.5, 1, 2, 4, and 6 months after the end of the 7 day infusion period. RNA was collected from the spinal cords and analyzed by northern blot. As shown in the graph below, the effect of ISIS396443 infusion persisted for 6 months after infusion, as shown in FIG. 2. This long duration of effect has several possible explanations. It may reflect stability of ISIS396443, stability of the corrected SMN protein and/or that the dose was high enough that even after loss of compound to metabolism, the remaining dose continued to provide benefit. Thus, these data may support administration of lower doses as well as infrequent doses.

EXAMPLE 5

Administration of Antisense Compounds by Continuous Intracerebroventricular (ICV) Infusion Using a micro-osmotic pump (Azlet Osmotic Pumps, Cupertino, Calif., USA), ISIS396443 was delivered into cerebrospinal fluid (CSF) through the right lateral ventricle in adult type-III Smn+/− or Smn−/− SMA mice with a human SMN2 transgene (Taiwan strain). Dose-response studies revealed that intracerebroventricular (ICV) infusion of the ISIS396443 increased SMN2 exon 7 inclusion in spinal cord to ~90%, compared to ~10% in saline-treated mice. Western blotting and immunohistochemical analysis demonstrated a robust increase of the human transgenic SMN protein levels in spinal-cord motor neurons. These results indicate that CNS infusion of antisense oligonucleotide ISIS396443 can rescue the SMA condition because exclusion of exon 7 is associated with the SMA phenotype.

EXAMPLE 6

Embryonic Administration

A single ICV injection of either 20 µg or 10 µg of ISIS396443 was administered to embryonic Taiwan mice at day 15 of gestation (E15). Animals were sacrificed at day 7 after birth (P7). RNA was isolated from the lumbar spinal cord and analyzed by RT-PCR. The single embryonic administration of ISIS 396443 resulted in substantial exon 7 inclusion. These results indicate that treatment with antisense oligonucleotide ISIS396443 in utero can rescue the SMA condition because exclusion of exon 7 is associated with the SMA phenotype.

Figure 3:
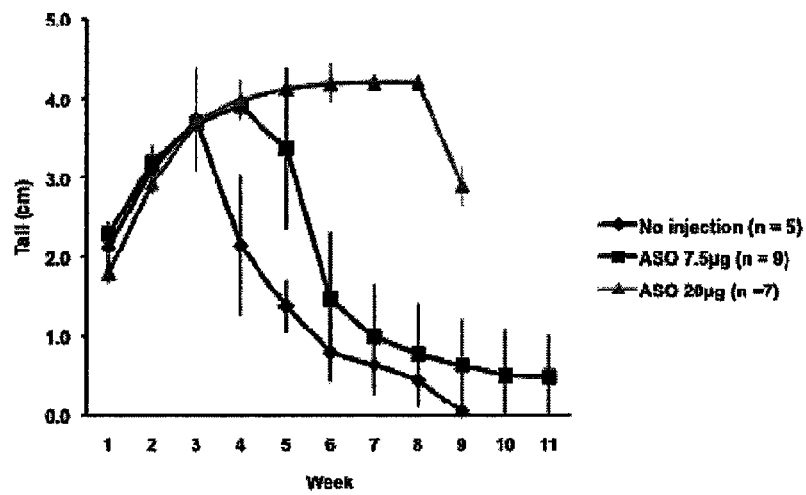
FIG. 3 shows the results from an experiments discussed in Example 6 measuring the effect of embryonic administration of ISIS396443 on tail-length in Taiwan strain of SMA mice.
Figure 3:
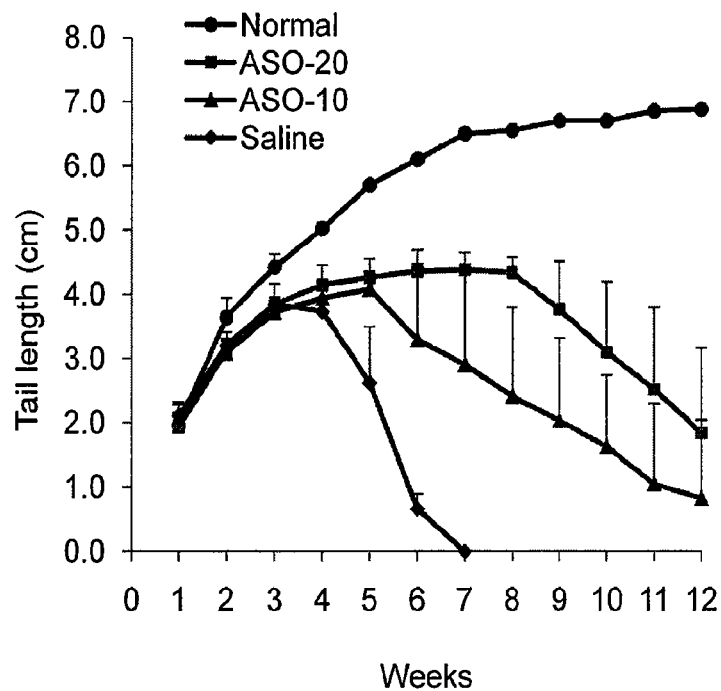

The above experiment was repeated and the animals were sacrificed at 11 weeks. Untreated Taiwan mice develop necrotic tails, which shorten over time. The single embryonic injection of 20 µg of ISIS396443 significantly delayed the onset of tail degradation, as shown in FIG. 3A. These results indicate that embryonic treatment with antisense oligonucleotide targeting SMN delays onset of SMA.

These results were confirmed in another study using the same conditions, except the doses tested were 20 µg and 10 µg of ISIS396443 and the study included normal mice for comparison. Results from that experiment are shown in FIG. 3B.

EXAMPLE 7

In Vivo Administration in the Delta-7 Mouse Model

Heterozygote (SMN$^{+/-}$, hSMN2$^{+/+}$, SMNΔ7$^{+/+}$) breeding pairs were mated and, on the day of birth (P0), newborn pups were treated with ISIS396443 (18-mer, SEQ ID NO. 1), ISIS396449 (15-mer, SEQ ID NO. 2), ISIS387954 (20-mer, SEQ ID NO. 7) or a scrambled control ASO (ISIS439273; 18-mer). Mice were injected bilaterally into the cerebral lateral ventricles for a total dose of 8 µg (4 µg in each lateral ventricle). All the injections were performed with a finely drawn glass micropipette needle as described (Passini et al, *J. Virol.* (2001) 75:12382-12392). Following the injections, the pups were toe-clipped and genotyped (Le et al., *Hum. Mol. Genet.* (2005) 14:845-857) to identify SMA (SMN$^{-/-}$, hSMN2$^{+/+}$, SMNΔ7$^{+/+}$), heterozygote, and wild type (SMN$^{+/+}$, hSMN2$^{+/+}$, SMNΔ7$^{+/+}$) mice. All the litters were culled to 7 pups to control for litter size on survival. Some of the litters were not injected in order to generate untreated control groups.

Widespread distribution of the 18-mer was detected in the spinal cord at 14 days post-injection in SMA mice, including the thoracic, lumbar, and cervical regions of the spinal cord. Furthermore, co-localization studies with ChAT confirmed the vast majority of the cells targeted by ISIS396443 in the spinal cord were motor neurons. No signal was detected in control, untreated mice.

Figure 4:
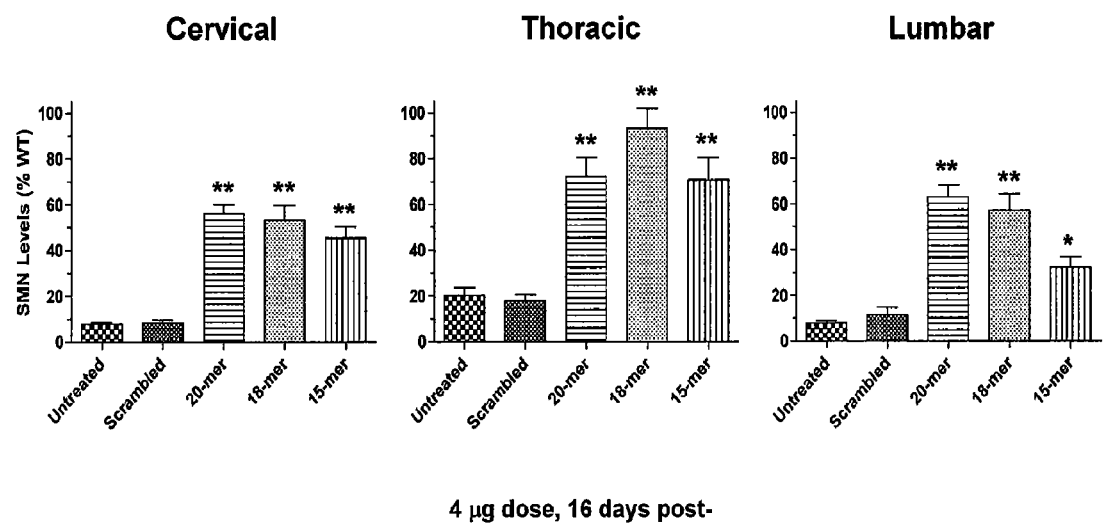
FIG. 4 shows results from western blots discussed in Example 7. The Y axis is the percent of SMN in the various samples that includes exon 7.

Western blot analysis at 14 days showed the amount of SMN in the brain and spinal cord were at 40-60% wild type levels, compared to 10% in untreated SMA controls. No signal above background was detected in control mice treated with a scrambled version of the ASO. Results of the western blots are provided in FIG. 4.

Figure 5:
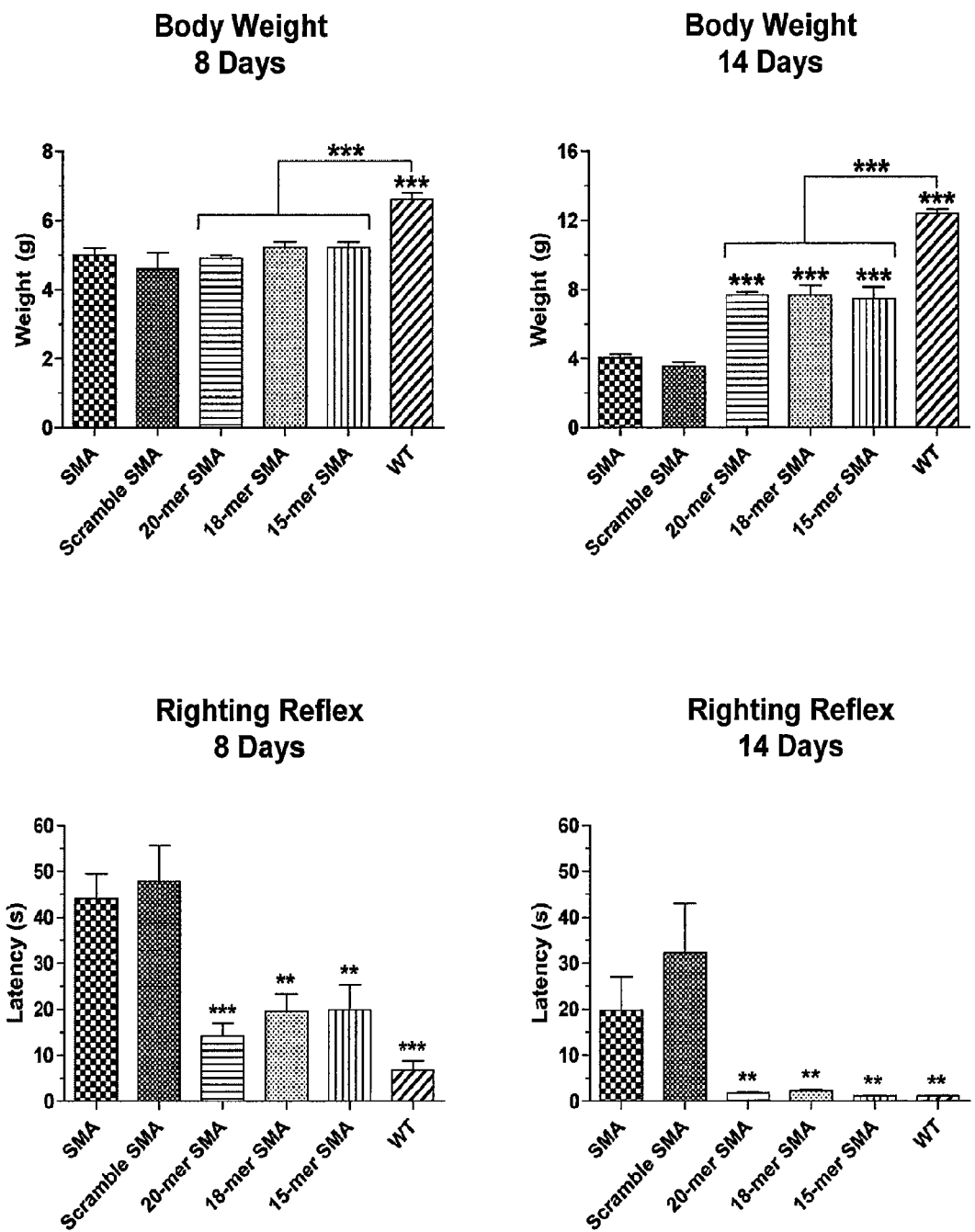
FIGS. 5 and 6 show results from experiments discussed in Example 7. A number of assessments of SMA mice (Taiwan strain) were performed following treatment with either an antisense compound or with a control oligonucleotide.
Figure 6:
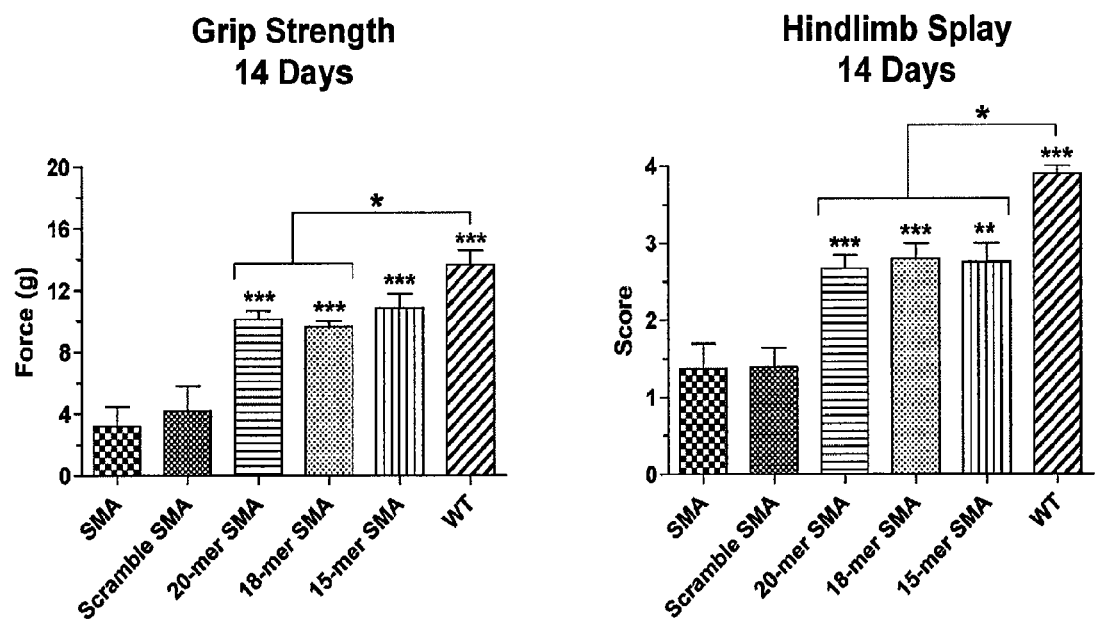

SMA mice treated with SMA ASOs also exhibited a significant increase in weight, ambulatory function (righting reflex and grip strength), and coordination (hindlimb splay) regardless of the length of the ASO as compared to untreated SMA mice or SMA mice treated with a scrambled ASO. No significant increase in body weight, ambulatory function (righting reflex and grip strength), or coordination was observed in SMA mice treated with a scrambled ASO as compared to untreated SMA mice. Results are provided in FIGS. 5 and 6.

Figure 7:
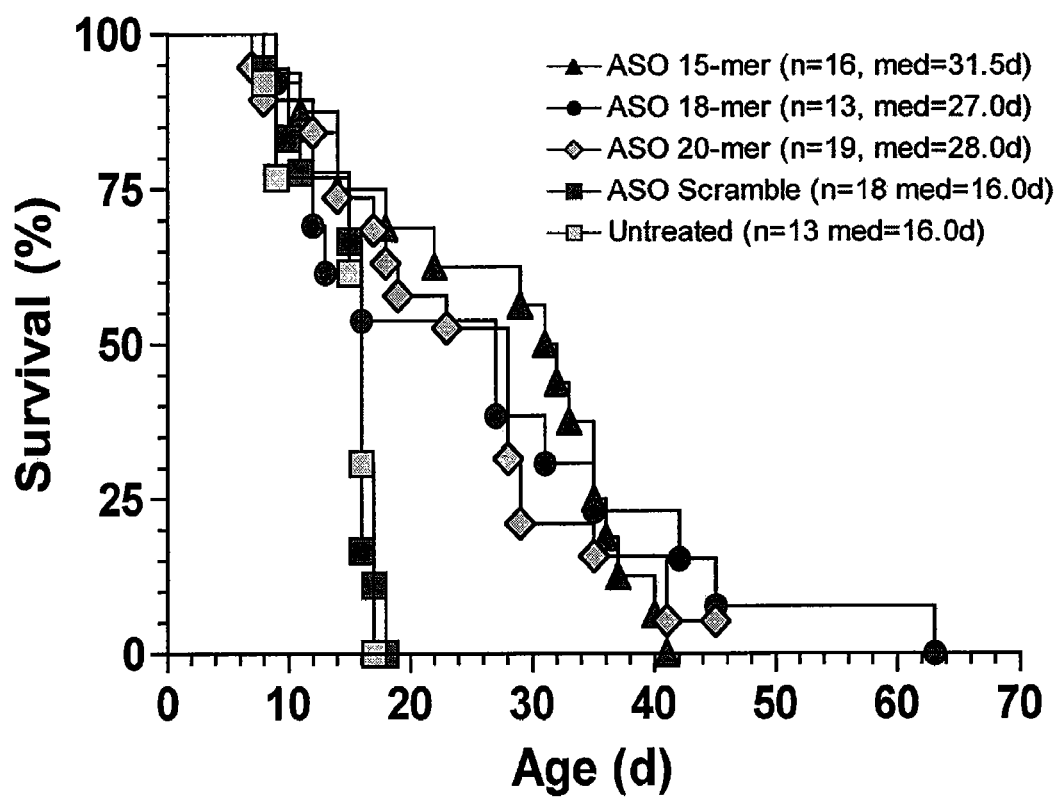
FIG. 7 shows a survival curve from an experiment discussed in Example 7.

Importantly, SMA mice treated with ASOs regardless of length of ASO produced a significant increase in median survival as shown in FIG. 7. Survival was from birth was 31.5 (15-mer), 27.0 (18-mer), and 28.0 (20-mer) days, compared to 16.0 days in untreated SMA controls. In contrast, SMA mice treated with an 18-mer scrambled control did not improve survival. These results demonstrate that treatment with antisense oligonucleotide targeting SMN treatment increases lifespan in SMA affected subjects.

Figure 8:
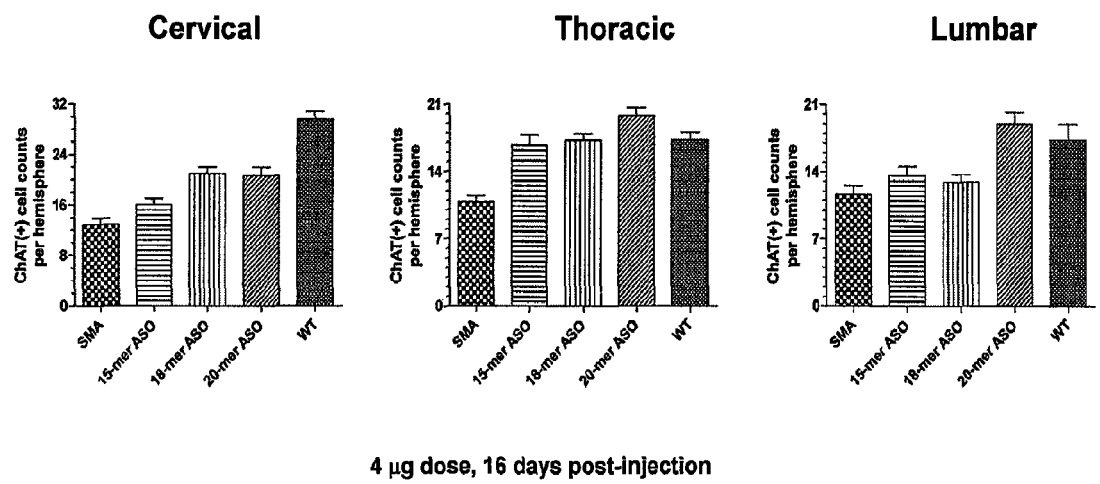
FIG. 8 shows results from an assessment of the number of motor neurons in different portions of the spinal cord following treatment with an antisense compound or with a control oligonucleotide, as discussed in Example 7.

The SMA ASOs also increased motor neuron cell counts in the spinal cord as shown in FIG. 8.

Figure 9:
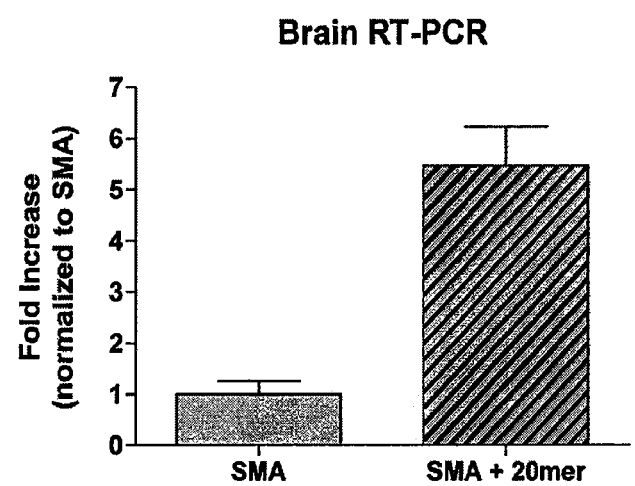
FIG. 9 shows results from an assessment of full SMN RNA (including exon 7) in animals treated with antisense as discussed in Example 7.

SMN RNA was measured by RT-PCR. Animals treated with SMA ASOs had increased SMN RNA levels compared to untreated SMA mice. Results from mice treated with the 20-mer ASO compared to untreated SMA mice are shown in FIG. 9.

Figure 10:
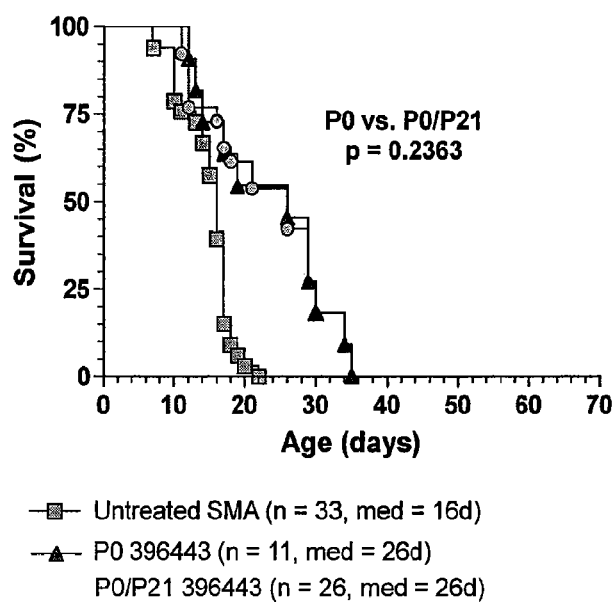
FIG. 10 shows a survival curve from an experiment discussed in Example 7 in which animals were either (1) untreated; (2) given a single dose of antisense compound at birth (Day P0); or (3) given a first dose at P0 and a second dose at day 21 (P21).

To determine whether survival could be further increased by administration of a second dose, the above experiment was repeated with an additional dose of 20 µg at day 21. Results are shown in FIG. 10. The graph above shows the effect of the first dose of 8 µg at day 0. At day P21, half of the treated mice were given a second treatment.

Figure 11:
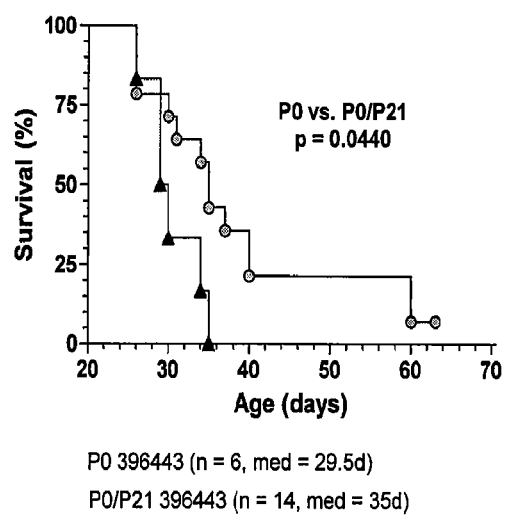
FIG. 11 shows a survival curve from an experiment described in Example 7 comparing animals that received the second dose with animals that received only the first dose.

The effect of the second treatment compared to mice that received only the first treatment is shown in FIG. 11. This result indicates that a second ICV treatment with antisense oligonucleotide further increases survival.

EXAMPLE 8

Activity in SMA Type III Mice

Two antisense compounds and one control compound were tested in a mouse model of SMA. The compounds are described in table below.

| ISIS# | Sequence | Description | SEQ ID |
|---|---|---|---|
| 396443 | TCACTTTCATAATGCTGG | Uniform 2'-MOE, full PS; 18-mer; complementary to intron 7 of human SMN2 | 1 |
| 449220 | ATTCACTTTCATAATGCTGG | Uniform 2-OMe; full PS; 20-mer; complementary to intron 7 of human SMN2 | 3 |
| 439272 | TTAGTTTAATCACGCTCG | Uniform 2'-MOE; full PS; 18-mer; control sequence | 4 |

Compounds Tested in Taiwan Strain SMA Mice

Taiwan strain of SMA type III mice were obtained from The Jackson Laboratory (Bar Harbor, Me.). These mice lack mouse SMN and are homozygous for human SMN2 (mSMN−/−; hSMN2+/+). These mice have been described in Hsieh-Li H M, et al., *Nature Genet.* 24, 66-70 2000.

Mice were treated with 3, 10, 30, or 100 μg of ISIS396443 or ISIS449220 per day or with 30 or 100 μg of control compound ISIS439272 per day in phosphate buffered saline (PBS). Control mice were treated with PBS alone (dose of 0). All treatments were administered by intracerebroventricular (ICV) infusion using an Azlet 1007D osmotic pump. There were five animals for each dose, however, two of the mice from the highest dose of ISIS449220 died prior to completion of the study. Animals were sacrificed on day 9 (two days after final dose) and brain and lumbar sections of the spinal cords were collected from each animal. Real time PCR was performed on each sample to determine the amount of human SMN2 message including exon 7 ((+)exon 7) and the amount of human SMN2 message lacking exon 7((−)exon 7). Real time PCR was also performed to determine the expression levels of allograft inflammatory factor (AIF1) and glyceraldehyde 3-phosphate dehyrogenase (GADPH).

Expression levels for (+)exon 7 and (−)exon 7 were normalized to GADPH levels. Those normalized expression levels were then divided by the GADPH-normalized levels from the PBS treated control mice. The resulting fold-control values are reported in Table 17, below. Data represent mean fold of control for all five mice in each group, except the highest dose of ISIS449220, which represent the 3 surviving mice.

Administration of ISIS396443 resulted in a striking increase in inclusion of exon 7. At 10 μg/day, ISIS396443 resulted in nearly twice as much (1.8 fold) exon 7 retained SMN2 message in brain, and in lumbar spinal cord it was more than twice as much compared to untreated control.

Ability of Antisense Compounds to Alter Splicing in SMA Mice

| | | Brain | | Lumbar Cord | |
|---|---|---|---|---|---|
| Compound | Dose (μg/day) | (+)exon 7 | (−)exon 7 | (+)exon 7 | (−)exon 7 |
| 396443 (2'-MOE) | 0 | 1.0 | 1.0 | 1.0 | 1.0 |
| | 3 | 1.3 | 1.0 | 1.4 | 1.0 |
| | 10 | 1.8 | 0.7 | 2.1 | 0.6 |
| | 30 | 2.4 | 0.6 | 3.4 | 0.3 |
| | 100 | 3.0 | 0.3 | 3.8 | 0.1 |
| 449220 (2'-OMe) | 0 | 1.0 | 1.0 | 1.0 | 1.0 |
| | 3 | 0.9 | 1.1 | 1.0 | 1.1 |
| | 10 | 1.0 | 1.1 | 1.0 | 1.2 |
| | 30 | 1.0 | 1.2 | 1.1 | 1.2 |
| | 100* | 1.0 | 1.0 | 1.2 | 1.1 |
| 439272 Control | 0 | 1.0 | 1.0 | 1.0 | 1.0 |
| | 30 | 1.0 | 1.1 | 0.9 | 1.1 |
| | 100 | 1.0 | 1.0 | 1.0 | 1.0 |

*data from only 3 mice for this dose

Expression of allograft inflammatory factor (AIF1) was tested as a measure of inflammation. After normalization of all samples to (GADPH), the ratio of AIF1 for each treatment group was divided by the value for the PBS control. ISIS396443 resulted in no increase in AIF1, even at the highest dose. ISIS449220 resulted in increased AIF1 in both brain and lumbar spinal cord. Data in Table 18 represent mean fold of control for all five mice in each group, except the highest dose of ISIS449220, which represent the 3 surviving mice.

Toxicity of antisense compounds in SMA Mice

| | | AIF-1/GAPDH | |
|---|---|---|---|
| Compound | Dose (μg/day) | Brain | Lumbar |
| 396443 (2'-MOE) | 0 | 1.0 | 1.0 |
| | 3 | 10 | 1.0 |
| | 10 | 1.1 | 1.2 |
| | 30 | 1.0 | 1.0 |
| | 100 | 0.9 | 1.0 |
| 449220 (2'-OMe) | 0 | 1.0 | 1.0 |
| | 3 | 1.0 | 1.0 |
| | 10 | 1.0 | 1.8 |
| | 30 | 1.2 | 2.9 |
| | 100* | 1.8 | 3.3 |
| 439272 Control | 0 | 0.9 | 0.9 |
| | 30 | 0.9 | 1.0 |
| | 100 | 0.9 | 1.2 |

*data from only 3 mice for this dose

EXAMPLE 9

Administration to Monkeys

Cynomolgus monkeys were used to assess distribution of ISIS395443 at different doses and routes of administration. ISIS396443 was administered to 2 monkeys. One monkey received a dose of 3 mg by ICV infusion and the other monkey received a dose of 3 mg by IT infusion. Both infusions were delivered over a 24 hour period. The monkeys were sacrificed and tissues were harvested 96 hours after the end of the infusion period. The concentration of ISIS396443 was measured in samples from Cervical, Thoracic, and Lumbar sections of the spinal cord. Results are summarized in the table below.

| Animal # | Dose | Route | Tissue | Concentration of ISIS396443 (µg/g) |
|---|---|---|---|---|
| 1 | 3 mg over 24 hours | ICV infusion | Cervical | 21.5 |
|   |   |   | Thoracic | 9.4 |
|   |   |   | Lumbar | 23.9 |
| 2 | 3 mg over 24 hours | IT infusion | Cervical | 12.5 |
|   |   |   | Thoracic | 22.6 |
|   |   |   | Lumbar | 42.6 |

Since cynololgus monkeys are approximately 3 kg, this dose is about 1 mg/kg.

To further assess distribution of ISIS39644, twenty-six monkeys were divided into six groups as provided in the table below.

| Group | Dose | Route | Concentration of compound (mg/ml) | Duration of infusion | Day sacrificed | Number of monkeys |
|---|---|---|---|---|---|---|
| 1 | 0 | ICV | 0 | 14 days | Day 19 | 2M/2F |
| 2 | 3 mg | ICV | 0.09 | 14 days | Day 19 | 2M/2F |
| 3 | 3 mg | IT | 1.25 | 1 day | Day 6 | 3M/2F |
| 4 | 3 mg | IT | 0.42 | 3 days | Day 8 | 2M/2F |
| 5 | 3 mg | IT | 0.18 | 7 days | Day 12 | 3M/2F |
| 6 | 3 mg | IT | 0.09 | 14 days | Day 19 | 2M/2F |

Infusion rate for all groups was 100 µL/hour. All monkeys received a total of 3 mg of ISIS39644 in saline, except for group 1, which received saline only. Monkeys were sacrificed and tissues were harvested 5 days after the end of infusion.

Figure 12:
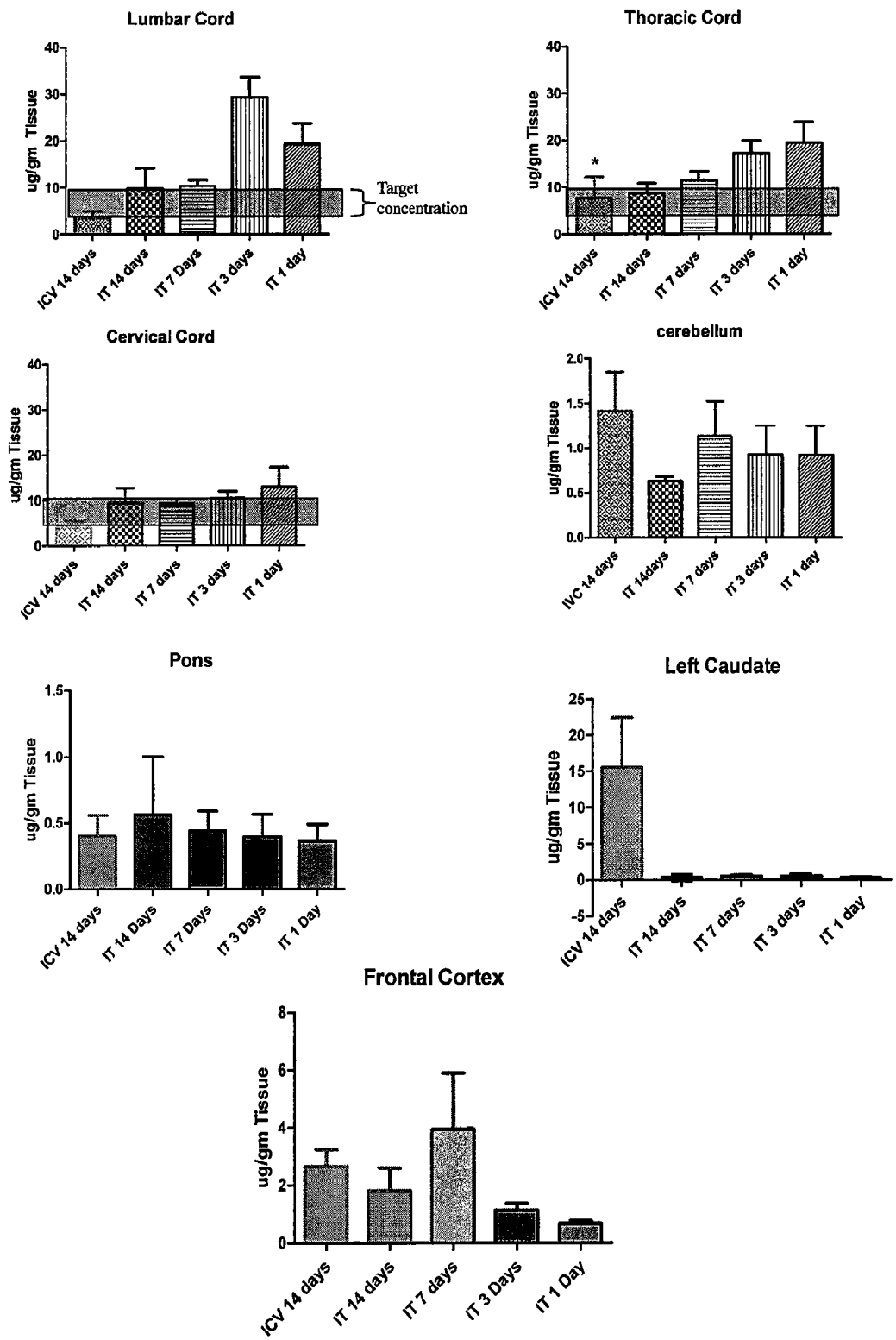
FIG. 12 shows results from an experiment discussed in Example 9 in which antisense compound was administered to monkeys by intrathecal infusion and concentration of the compound was assessed in different tissues 96 hours later.
Figure 13:
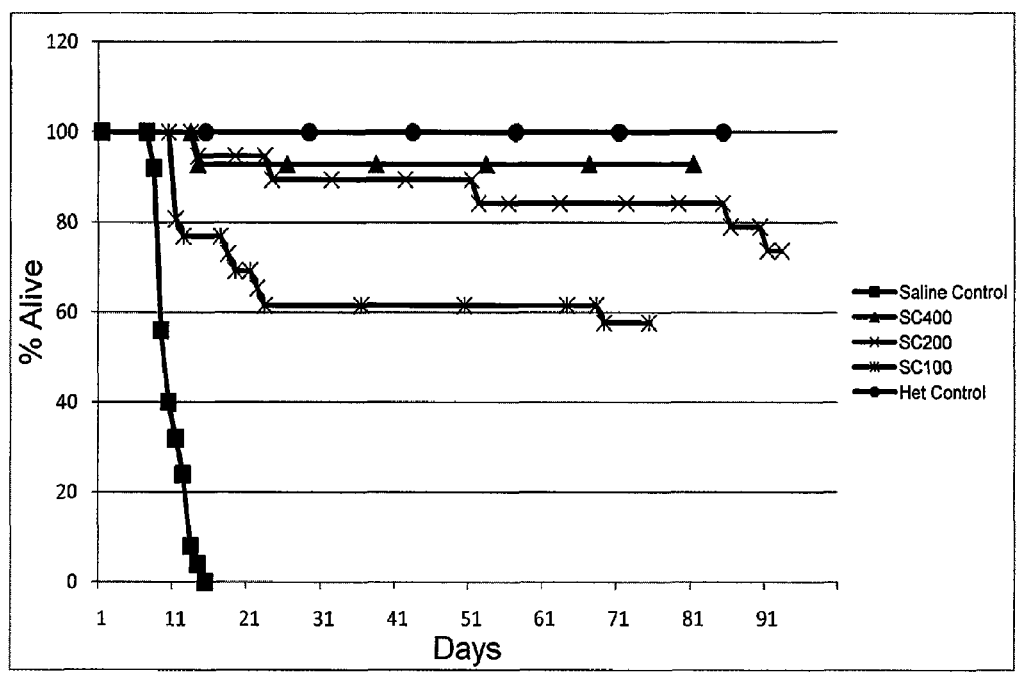
FIG. 13 shows a survival curve for experiments discussed in Example 12, in which different doses of antisense compound were administered to severe SMA mice by subcutaneous injection.

Concentrations of ISIS39644 in tissue samples from the monkeys were evaluated using standard techniques. Summaries of the results are provided in the graphs in FIG. 12. Samples were also evaluated by histology. The histology did not show any adverse effect of treatment and confirmed presence of ISIS396443. There was no evidence of Purkinje cell loss.

Rapid infusion appeared to have more ISIS396443 than slower infusion. These results suggest that faster infusion rates or bolus injection may be preferred in certain embodiments. Since bolus administration has certain practical advantages over infusion, in certain embodiments, it is the preferred method of administration into the CSF. In certain embodiments, the preferred method of administration into the CSF is by bolus IT injection.

EXAMPLE 10

Generation of a Mouse Model of Severe SMA and ICV Treatment

Mice having a severe SMA phenotype (sSMA mice) were generated. Homozygote sSMA mice carry 2 copies of human SMN2 and no mouse SMN. The average lifespan is about 10 days. In addition, the SMA mice are smaller and have shorter tails. Heterozygotes carry mouse SMN and develop normally.

To study the effect of antisense compounds in these sSMA mice, 20 µg of ISIS396443 was injected ICV at day P1. Treatment resulted in an increase in average survival from 9.9 days (saline treated control) to 16.7 days. RT-PCR analysis showed increased full-length SMN RNA in tissues from the treated mice.

EXAMPLE 11

Systemic Administration of ISIS 396443 sSMA mice and healthy heterozygote control mice were divided into groups to study the effect of ISIS396443 by bolus ICV injection and/or bolus subcutaneous injection (SC) as follows:

Group 1—ICV+SC
  One ICV injection of 20 µg at P1 or P2 (day 1 or 2 after birth); and two subcutaneous injections of 50 µg/g delivered between P0 and P3.
Group 2—SC+SC
  Two SC injections of 50 µg/g delivered between P0 and P3; and one subcutaneous injection of 50 µg/g delivered between P5 and P6; and subcutaneous injection of 50 µg/g delivered between P9 and P10.
Group 3—SC
  Two SC injections of 50 µg/g delivered between P0 and P3.
Group 4—SMA saline control
  One ICV injection of saline at P1 or P2; and two subcutaneous injections of saline delivered between P0 and P3.
Group 5—Heterozygous Control
  One ICV injection of 20 µg at P1 or P2; and two subcutaneous injections of 50 µg delivered between P0 and P3 of heterozygous mice.

Each group included from 14 to 22 mice. Survival (in days) for individual mice in each group is provided in the table, below. Many mice in this study remain alive at the time that this patent application is being prepared. Thus, a value proceeded by a ">" indicates that the mouse has lived that number of days and is still alive.

| Mouse | Group 1 ICV + SC | Group 2 SC + SC | Group 3 SC | Group 4 Saline | Group 5 Het |
|---|---|---|---|---|---|
| 1 | >141 | >130 | >103 | 8 | >146 |
| 2 | >141 | 127 | 94 | 8 | >146 |
| 3 | 22 | >114 | 61 | 8 | >146 |
| 4 | >140 | 73 | >103 | 8 | >146 |
| 5 | 117 | 27 | >103 | 8 | >145 |
| 6 | >124 | 27 | >103 | 8 | >145 |
| 7 | >111 | 18 | 34 | 8 | >145 |
| 8 | >111 | >102 | 26 | 8 | >145 |
| 9 | >111 | >98 | 31 | 8 | >145 |
| 10 | >111 | >98 | 69 | 9 | >144 |
| 11 | 29 | >102 | 69 | 9 | >144 |
| 12 | >110 | >102 | 67 | 9 | >144 |
| 13 | >110 | >102 | >91 | 9 | >144 |
| 14 | >110 | >102 | >90 | 9 | >143 |
| 15 | >110 | ND | >90 | 9 | >143 |
| 16 | >108 | ND | >90 | 9 | >143 |
| 17 | >108 | ND | >90 | 10 | >129 |
| 18 | >109 | ND | 86 | 10 | >129 |
| 19 | 18 | ND | >75 | 10 | >129 |
| 20 | ND | ND | 69 | 10 | ND |
| 21 | ND | ND | 18 | 11 | ND |
| 22 | ND | ND | >71 | 12 | ND |
| 23 | ND | ND | ND | 12 | ND |
| 24 | ND | ND | ND | 13 | ND |

| Mouse | Group 1 ICV + SC | Group 2 SC + SC | Group 3 SC | Group 4 Saline | Group 5 Het |
|---|---|---|---|---|---|
| 25 | ND | ND | ND | 13 | ND |
| 26 | ND | ND | ND | 14 | ND |

EXAMPLE 12

Dose-Response of SC Administration

Survival of sSMA mice receiving different doses of subcutaneous ISIS396443 was assessed by the following dosing groups.

Group 1—SC400 (dose ranges from 80 mg/kg to 180 mg/kg)

Two SC injections totaling 400 µg per mouse delivered between P0 to P3, first dose was 150 µg at P0 or P1 (volume of 3 µl) and second was 250 µg delivered P2 or P3 (volume of 5 µl).

Group 2—SC200 (dose ranges from 40 mg/kg to 90 mg/kg)

Two SC injections totaling 200 µg per mouse delivered between P0 and P3, first dose was 75 µg at P0-P1 (volume of 1.5 µl) and second was 125 µg delivered P2 or P3 (volume of 2.5 µl).

Group 3—SC100 (dose ranges from 20 mg/kg to 45 mg/kg)

Two SC injections totaling 100 µg per mouse delivered between P0 and P3, first dose was 40 µg at P0 or P1 (volume of 2 µl) and second was 60 µg delivered P2 or P3 (volume of 3 µl).

Group 4—SMA saline (negative controls)

Two SC injections of saline between P0 and P3, first was at P0 or P1 (volume of 5 µl) and second delivered P2 or P3 (volume of 5 µl).

Group 5—Heterozygous control (positive controls)

Mice without any treatment.

Each group included from 14 to 26 mice. Survival (in days) for individual mice in each group is provided in the table, below. Many mice in this study remain alive at the time that this patent application is being prepared. Thus, a value proceeded by a ">" indicates that the mouse has lived that number of days and is still alive.

| Mouse | Group 1 SC400 | Group 2 SC200 | Group 3 SC100 | Group 4 Saline | Group 5 Het |
|---|---|---|---|---|---|
| 1 | >82 | >93 | 11 | 8 | >87 |
| 2 | >82 | >91 | 11 | 8 | >87 |
| 3 | >82 | >91 | 11 | 9 | >87 |
| 4 | >82 | >91 | 11 | 9 | >87 |
| 5 | >82 | 14 | 11 | 9 | >87 |
| 6 | >82 | 25 | 12 | 9 | >87 |
| 7 | >82 | 92 | 18 | 9 | >86 |
| 8 | >82 | >93 | 19 | 9 | >86 |
| 9 | >82 | >93 | 22 | 9 | >86 |
| 10 | >82 | >90 | 69 | 9 | >86 |
| 11 | >82 | >90 | >77 | 9 | >86 |
| 12 | >80 | >91 | >77 | 10 | >86 |
| 13 | >80 | >91 | >77 | 10 | >86 |
| 14 | 25 | >90 | >77 | 10 | >86 |
| 15 | ND | >90 | >75 | 10 | >85 |
| 16 | ND | >90 | >74 | 11 | >85 |
| 17 | ND | 86 | >74 | 11 | >85 |
| 18 | ND | >90 | >74 | 12 | ND |
| 19 | ND | >52 | >74 | 12 | ND |
| 20 | ND | ND | >74 | 13 | ND |
| 21 | ND | ND | >74 | 13 | ND |
| 22 | ND | ND | >71 | 13 | ND |
| 23 | ND | ND | >49 | 13 | ND |
| 24 | ND | ND | >49 | 14 | ND |
| 25 | ND | ND | >49 | 15 | ND |
| 26 | ND | ND | 23 | ND | ND |

EXAMPLE 13

ICV Infusion vs. ICV Bolus

Administration by intracerebroventricular bolus injection (ICV bolus) was compared to administration by continuous intracerebroventricular infusion (ICV infusion). The SMA type III transgenic mice were dosed with ISIS387954. ICV infusion mice were given a total dose of 0 (PBS control), 87.5 µg, 175 µg, 350 µg, or 700 µg infused over 7 days and were sacrificed 2 days later. ICV bolus mice were given the same total doses, 0 (PBS control), 87.5 µg, 175 µg, 350 µg, or 700 µg, in a single ICV injection and were sacrificed 9 days later. There were 5 mice in each group. RNA was collected from the lumbar spinal cord and was analyzed by real time PCR. Intron 7 inclusion was normalized to the saline-treated controls. Results are summarized in the table below.

| Group | Dose | Fold increase in intron 7 inclusion relative to PBS |
|---|---|---|
| 1 | PBS (control) | 1.0 |
| 2 | 87.5 µg by ICV infusion over 7 days | 2.1 |
| 3 | 175 µg by ICV infusion over 7 days | 2.4 |
| 4 | 350 µg by ICV infusion over 7 days | 3.2 |
| 5 | 700 µg by ICV infusion over 7 days | 3.6 |
| 6 | PBS (control) | 1.0 |
| 7 | 87.5 µg by ICV bolus | 3.1 |
| 8 | 175 µg by ICV bolus | 3.7 |
| 9 | 350 µg by ICV bolus | 3.8 |
| 10 | 700 µg by ICV bolus | 3.8 |

In this experiment, the same dose when delivered by ICV bolus injection resulted in greater activity than when delivered by ICV infusion over 7 days.

Real time PCR was also performed to determine the expression levels of allograft inflammatory factor (AIF1) to assess inflammation. None of the samples from treated mice showed a significant difference from control mice.

EXAMPLE 14

Dose-Response by ICY Bolus

Administration by intracerebroventricular bolus was tested at additional doses. The transgenic mice were administered 0, 10.9 µg, 21.9 µg, 43.4 µg, 87.5 µg, or 175 µg of ISIS387954 by single bolus ICV injection and were sacrificed 9 days later as described in Example 13. Samples were collected from brain and from lumbar spinal cord. RNA was prepared and analyzed by RT-PCR for change in intron 7 inclusion and for change in AIF1. None of the samples showed a change in AIF1 compared to control. Results from intron 7 inclusion are summarized in the table below. The ED50 is at around 22 µg.

| Group | Dose | Fold increase in intron 7 inclusion relative to PBS | |
|---|---|---|---|
| | | Brain | Lumbar spinal cord |
| 1 | PBS (control) | 1.0 | 1.0 |
| 2 | 10.9 µg by ICV bolus | 2.4 | 2.2 |
| 3 | 21.9 µg by ICV bolus | 2.8 | 2.7 |
| 4 | 43.4 µg by ICV bolus | 3.2 | 3.4 |

-continued

| Group | Dose | Fold increase in intron 7 inclusion relative to PBS | |
|---|---|---|---|
| | | Brain | Lumbar spinal cord |
| 5 | 87.5 µg by ICV bolus | 3.5 | 3.4 |
| 6 | 175 µg by ICV bolus | 4.4 | 3.7 |

What is claimed is:

1. A method comprising administering by a bolus injection into the intrathecal space of a subject with infantile-onset type I spinal muscular atrophy (SMA) an antisense compound comprising an antisense oligonucleotide consisting of 18 linked nucleosides, wherein the oligonucleotide has a nucleobase sequence consisting of the nucleobase sequence SEQ ID NO: 1, wherein each internucleoside linkage of the oligonucleotide is a phosphorothioate linkage, wherein each nucleoside of the oligonucleotide is a 2'-MOE nucleoside, and wherein the administering of the antisense compound ameliorates at least one symptom of SMA in the subject.

2. The method of claim 1, wherein the antisense compound is administered at a dose from 0.5 to 10 milligrams of antisense compound per kilogram of body weight of the subject.

3. The method of claim 1, wherein inclusion of exon 7 of SMN2 mRNA in a motoneuron in the subject is increased.

4. The method of claim 1, wherein a 5 mg to 20 mg dose of antisense is administered.

* * * * *

UNITED STATES PATENT AND TRADEMARK OFFICE
CERTIFICATE OF CORRECTION

PATENT NO. : 8,980,853 B2
APPLICATION NO. : 13/380021
DATED : March 17, 2015
INVENTOR(S) : C. Frank Bennett et al.

Page 1 of 1

It is certified that error appears in the above-identified patent and that said Letters Patent is hereby corrected as shown below:

In the Claims

Column 55
Claim 4, Line 19, delete "antisense" and insert -- the antisense compound --.

Signed and Sealed this
Twenty-fifth Day of August, 2020

Andrei Iancu
*Director of the United States Patent and Trademark Office*

SEQUENCE LISTING

```
<160> NUMBER OF SEQ ID NOS: 24

<210> SEQ ID NO 1
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 1
tcactttcat aatgctgg                                                 18

<210> SEQ ID NO 2
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 2
tttcataatg ctggc                                                    15

<210> SEQ ID NO 3
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 3
tgctggcaga cttac                                                    15

<210> SEQ ID NO 4
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 4
cataatgctg gcaga                                                    15

<210> SEQ ID NO 5
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 5
tcataatgct ggcag                                                    15

<210> SEQ ID NO 6
<211> LENGTH: 15
```

```
<212> TYPE: DNA
<213> ORGANISM: Artificial Sequence
<220> FEATURE:
<223> OTHER INFORMATION: Synthetic Oligonucleotide

<400> SEQUENCE: 6
ttcataatgc tggca                                                    15

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
attcactttc ataatgctgg                                               20

<210> SEQ ID NO 8
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 8
ctttcataat gctgg                                                    15

<210> SEQ ID NO 9
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 9
tcataatgct gg                                                       12

<210> SEQ ID NO 10
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 10
actttcataa tgctg                                                    15

<210> SEQ ID NO 11
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 11
ttcataatgc tg                                                       12

<210> SEQ ID NO 12
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 12
```

```
cactttcata atgct                                                    15

<210> SEQ ID NO 13
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 13
tttcataatg ct                                                       12

<210> SEQ ID NO 14
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 14
tcactttcat aatgc                                                    15

<210> SEQ ID NO 15
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 15
ctttcataat gc                                                       12

<210> SEQ ID NO 16
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 16
ttcactttca taatg                                                    15

<210> SEQ ID NO 17
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 17
actttcataa tg                                                       12

<210> SEQ ID NO 18
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 18
attcactttc ataat                                                    15

<210> SEQ ID NO 19
<211> LENGTH: 12
<212> TYPE: DNA
<213> ORGANISM: Artificial Sequence
```

```
<220> FEATURE:
<223> OTHER INFORMATION: Synthetic Oligonucleotide

<400> SEQUENCE: 19
cactttcata at                                                          12

<210> SEQ ID NO 20
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 20
gattcacttt cataa                                                       15

<210> SEQ ID NO 21
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 21
tcactttcat aa                                                          12

<210> SEQ ID NO 22
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 22
ttcactttca ta                                                          12

<210> SEQ ID NO 23
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 23
attcactttc at                                                          12

<210> SEQ ID NO 24
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 24
agtaagattc acttt                                                       15
```